(12) United States Patent
Herold et al.

(10) Patent No.: US 8,071,774 B2
(45) Date of Patent: Dec. 6, 2011

(54) HETEROCYCLIC SPIRO-COMPOUNDS AS ALDOSTERONE SYNTHASE INHIBITORS

(75) Inventors: Peter Herold, Basel (CH); Robert Mah, Muttenz (CH); Vincenzo Tschinke, Binningen (CH); Aleksandar Stojanovic, Basel (CH); Christiane Marti, Rheinfelden (CH); Nathalie Jotterand, Basel (CH); Christoph Schumacher, Bettingen (CH); Michael Quirmbach, Basel (CH)

(73) Assignee: Novartis AG, Basel (CH)

( * ) Notice: Subject to any disclaimer, the term of this patent is extended or adjusted under 35 U.S.C. 154(b) by 1010 days.

(21) Appl. No.: 11/921,311

(22) PCT Filed: May 30, 2006

(86) PCT No.: PCT/EP2006/062695
§ 371 (c)(1),
(2), (4) Date: Nov. 30, 2007

(87) PCT Pub. No.: WO2006/128852
PCT Pub. Date: Dec. 7, 2006

(65) Prior Publication Data
US 2010/0010015 A1 Jan. 14, 2010

(51) Int. Cl.
*C07D 491/20* (2006.01)
*A61K 31/438* (2006.01)
(52) U.S. Cl. .......................... 546/19; 514/278
(58) Field of Classification Search .............. 546/19; 514/278
See application file for complete search history.

(56) References Cited

FOREIGN PATENT DOCUMENTS

| WO | 2004/014914 | 2/2004 |
|---|---|---|
| WO | 2004/046145 | 6/2004 |

OTHER PUBLICATIONS

Dorwald F. A. Side Reactions in Organic Synthesis, 2005, Wiley: VCH, Weinheim p. IX of Preface.*
International Search Report issued Oct. 24, 2006 in the International (PCT) Application PCT/EP2006/062695 of which the present application is the U.S.National Stage.
PCT Written Opinion for International (PCT) Application PCT/EP2006/062695.

* cited by examiner

*Primary Examiner* — Rita Desai
(74) *Attorney, Agent, or Firm* — Wenderoth, Lind & Ponack, L.L.P.

(57) ABSTRACT

The patent application relates to new heterocyclic compounds of the general formula (I) in which A, R, $R^1$, $R^2$, U, V, W, X, Y, Z, n and p have the definitions elucidated in more detail in the description, to a process for preparing them and to the use of these compounds as medicaments, particularly as aldosterone synthase inhibitors.

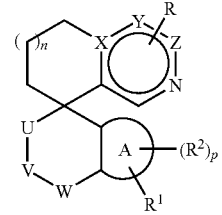

(I)

9 Claims, No Drawings

HETEROCYCLIC SPIRO-COMPOUNDS AS ALDOSTERONE SYNTHASE INHIBITORS

FIELD OF THE INVENTION

The invention relates to new heterocycles, to processes for preparing the compounds according to the invention, to pharmaceutical products comprising them, and to their use as active pharmaceutical ingredients, in particular as aldosterone synthase inhibitors.

DETAILED DESCRIPTION OF THE INVENTION

The present invention first provides compounds of the general formula

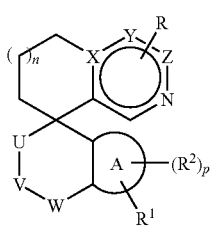

(I)

in which
A is aryl or heterocyclyl;
U is —$C(R^3)(R^4)$—, —O—, —$S(O)_m$—, —$N(R^5)$— or a bond;
V is —$C(R^3)(R^4)$— or
  a) if U is either a bond or —$C(R^3)(R^4)$—, V is alternatively —O—, —$S(O)_m$— or —$N(R^5)$—,
  b) if U is —$S(O)_m$—, V is alternatively —$N(R^5)$—, or
  c) if U is —$N(R^5)$—, V is alternatively —$S(O)_m$—;
W is —$C(R^3)(R^4)$— or
  a) if U is either a bond or —$C(R^3)(R^4)$— and V is —$C(R^3)(R^4)$—, W is alternatively —O—, —$S(O)_m$— or —$N(R^5)$—,
  b) if U is either a bond or —$C(R^3)(R^4)$— and V is —$S(O)_m$—, W is alternatively —$N(R^5)$—,
  c) if U is either a bond or —$C(R^3)(R^4)$— and V is —$N(R^5)$—, W is alternatively —$S(O)_m$—, or
  d) if U is —$N(R^5)$— and V is —C(O)—, W is alternatively —$N(R^5)$—;
X is C or, if Z is a bond, is alternatively N;
Y is C or, if Z is C, is alternatively N;
Z is C or a bond;
  the ring containing Y being maximum unsaturated;
R is hydrogen, $C_1$-$C_8$-alkyl, $C_1$-$C_8$-alkoxy-$C_0$-$C_4$-alkyl, halogen, tri-$C_1$-$C_4$-alkylsilyl, deuterium or trifluoromethyl;
$R^1$ is $C_1$-$C_8$-alkyl, $C_0$-$C_8$-alkylcarbonyl, amino, mono- or di-$C_1$-$C_8$-alkylamino, $C_0$-$C_8$-alkylcarbonylamino, $C_0$-$C_8$-alkylcarbonyl-$C_1$-$C_8$-alkylamino, carbamoyl, mono- or di-$C_1$-$C_8$-alkylaminocarbonyl, carboxyl, carboxy-$C_1$-$C_4$-alkyl, halogen, cyano, oxo, trifluoromethyl, $C_1$-$C_8$-alkoxy, $C_1$-$C_8$-alkoxycarbonyl, heterocyclyl or aryl, which radicals may be substituted by 1-4 $C_1$-$C_8$-alkyl, $C_0$-$C_8$-alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl, aryl or heterocyclyl;
$R^2$ a) is, independently of one another, hydrogen, $C_1$-$C_8$-alkyl, $C_0$-$C_8$-alkylcarbonyl, amino, mono- and di-$C_1$-$C_8$-alkylamino, $C_0$-$C_8$-alkylcarbonylamino, $C_0$-$C_8$-alkylcarbonyl-$C_1$-$C_8$-alkylamino, carbamoyl, mono- or di-$C_1$-$C_8$-alkylaminocarbonyl, carboxyl, carboxy-$C_1$-$C_4$-alkyl, halogen, cyano, oxo, trifluoromethyl, trifluoromethoxy, $C_1$-$C_8$-alkoxy, $C_1$-$C_8$-alkoxycarbonyl, heterocyclyl or aryl, which radicals may be substituted by 1-4 $C_1$-$C_8$-alkyl, $C_0$-$C_8$-alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl, aryl or heterocyclyl; or
  b) together with $R^1$ is a fused-on 5-6-membered heterocyclic ring;
$R^3$ is hydrogen or $C_1$-$C_8$-alkyl;
$R^4$ a) is hydrogen or $C_1$-$C_8$-alkyl; or
  b) together with $R^3$ is oxo;
$R^5$ is hydrogen, $C_1$-$C_8$-alkyl or $C_0$-$C_8$-alkylcarbonyl;
m is a number 0, 1 or 2;
n is a number 0, 1 or 2;
p is a number 1, 2 or 3;
and their salts, preferably their pharmaceutically useful salts.

The aryl term stands for an aromatic hydrocarbon which contains generally 5-14, preferably 6-10, carbon atoms and is for example phenyl, or naphthyl, e.g. 1- or 2-naphthyl. Preference is given to aryl having 6-10 carbon atoms, particularly phenyl or 1- or 2-naphthyl. The stated radicals may be unsubstituted or may be substituted one or more times, such as once or twice, in which case the substituent may be in any position, such as in the o, m or p position of the phenyl radical or in the 3 or 4 position of the 1- or 2-naphthyl radical, and there may also be two or more identical or different substituents.

The heterocyclyl term stands for a saturated or unsaturated, 4-8-membered, more preferably 5-membered, monocyclic ring system, for a saturated or unsaturated, 7-12-membered, more preferably 9-10-membered, bicyclic ring system, and alternatively for a saturated or unsaturated 7-12-membered tricyclic ring system, in each case containing an N, O or S atom in at least one ring, it also being possible for an additional N, O or S atom to be present in one ring, and the heteroatoms being separated preferably by at least one C atom. The stated radicals may be unsubstituted or may be substituted one or more times, such as once or twice, and there may also be two or more identical or different substituents.

Unsaturated monocyclic heterocyclyl-$C_0$-$C_4$-alkyl is for example furyl, pyrrolyl, thiophenyl, thiazolyl or oxazolyl.

Saturated monocyclic heterocyclyl-$C_0$-$C_4$-alkyl is for example pyrrolidinyl.

Unsaturated bicyclic heterocyclyl-$C_0$-$C_4$-alkyl is for example 4,5,6,7-tetrahydroisobenzofuranyl, 4,5,6,7-tetrahydrobenzothiazolyl, benzofuranyl, benzothiophenyl, isoquinolyl or quinolyl.

$C_1$-$C_8$-Alkyl can be linear or branched and/or bridged and is for example methyl, ethyl, propyl, isopropyl, butyl, isobutyl, secondary-butyl, tertiary-butyl, or a pentyl, hexyl or heptyl group.

$C_1$-$C_8$-Alkoxy is for example $C_1$-$C_5$-alkoxy, such as methoxy, ethoxy, propyloxy, isopropyloxy, butyloxy, isobutyloxy, secondary-butyloxy, tertiary-butyloxy or pentyloxy, but can also be a hexyloxy or heptyloxy group.

$C_1$-$C_8$-Alkoxycarbonyl is preferably $C_1$-$C_4$-alkoxycarbonyl, such as methoxycarbonyl, ethoxycarbonyl, propyloxycarbonyl, isopropyloxycarbonyl, butyloxycarbonyl, isobutyloxycarbonyl, secondary-butyloxycarbonyl or tertiary-butyloxycarbonyl.

$C_0$-$C_8$-Alkylcarbonyl is for example formyl, acetyl, propionyl, propylcarbonyl, isopropylcarbonyl, butylcarbonyl, isobutylcarbonyl, secondary-butylcarbonyl or tertiary-butylcarbonyl.

Halogen is for example fluoro, chloro, bromo or iodo.

Carboxy-$C_1$-$C_4$-alkyl is for example carboxymethyl, 2-carboxyethyl, 2- or 3-carboxypropyl, 2-carboxy-2-methylpropyl, 2-carboxy-2-ethylbutyl or 4-carboxybutyl, especially carboxymethyl.

Mono- or di-$C_1$-$C_8$-alkylamino is for example $C_1$-$C_4$-alkylamino, such as methylamino, ethylamino, propylamino or butylamino, or di-$C_1$-$C_4$-alkylamino, such as dimethylamino, N-methyl-N-ethylamino, diethylamino, N-methyl-N-propylamino or N-butyl-N-methylamino.

Mono- or di-$C_1$-$C_8$-alkylaminocarbonyl is for example $C_1$-$C_4$-alkylaminocarbonyl, such as methylaminocarbonyl, ethylaminocarbonyl, propylaminocarbonyl or butylaminocarbonyl, or di-$C_1$-$C_4$-alkylaminocarbonyl, such as dimethylaminocarbonyl, N-methyl-N-ethylamino-carbonyl, diethylaminocarbonyl, N-methyl-N-propylaminocarbonyl or N-butyl-N-methylamino-carbonyl.

$C_0$-$C_8$-Alkylcarbonylamino is for example formylamino, acetylamino, propionylamino, propylcarbonylamino, isopropylcarbonylamino, butylcarbonylamino, isobutylcarbonylamino, secondary-butylcarbonylamino or tertiary-butylcarbonylamino.

$C_0$-$C_8$-Alkylcarbonyl-$C_1$-$C_8$-alkylamino is for example formyl-, acetyl-, propionyl-, propylcarbonyl-, isopropylcarbonyl-, butylcarbonyl-, isobutylcarbonyl-, secondary-butylcarbonyl- or tertiary-butylcarbonyl-methylamino, formyl-, acetyl-, propionyl-, propylcarbonyl-, isopropylcarbonyl-, butylcarbonyl-, isobutylcarbonyl-, secondary-butylcarbonyl- or tertiary-butylcarbonyl-ethylamino, formyl-, acetyl-, propionyl-, propylcarbonyl-, isopropylcarbonyl-, butylcarbonyl-, isobutylcarbonyl-, secondary-butylcarbonyl- or tertiary-butylcarbonyl-propylamino or formyl-, acetyl-, propionyl-, propylcarbonyl-, isopropylcarbonyl-, butylcarbonyl-, isobutylcarbonyl-, secondary-butylcarbonyl- or tertiary-butylcarbonyl-butylamino.

The groups of compounds specified below should not be considered as being closed; on the contrary, parts of these groups of compounds may be replaced by one another or by the definitions given above, or may be omitted, in a meaningful way, such as in order to replace more general definitions by more specific definitions.

Preferred compounds of the formula (I) are compounds of the general formulae

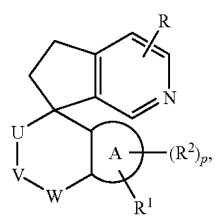
(Ia)

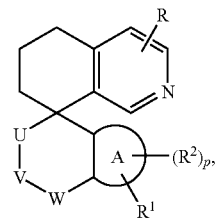
(Ib)

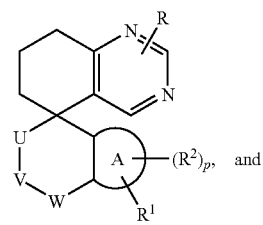
(Ic)

and

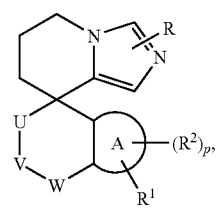
(Id)

the definitions of the substituents A, R, $R^1$, $R^2$, U, V, W and p being as specified for compounds of the formula (I).

A is preferably aryl and more preferably phenyl.

R is more preferably hydrogen or deuterium.

$R^1$ is preferably $C_1$-$C_8$-alkyl, $C_0$-$C_8$-alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl or heterocyclyl, very preferably formyl, acetyl, cyano or unsubstituted or mono-substituted furyl, pyrrolidinyl, thiophenyl, thiazolyl or oxazolyl.

$R^2$ is, independently of one another, preferably hydrogen, halogen, cyano, trifluoromethyl, trifluoromethoxy, or $C_1$-$C_8$-alkyl, very preferably hydrogen, halogen, cyano or $C_1$-$C_8$-alkyl;

n is preferably a number 0 or 1.

p is preferably the number 1.

Preferred substituents for aryl or heterocyclyl are halogen, cyano, trifluoromethyl, heterocyclyl or $C_1$-$C_8$-alkylcarbonyl. Very preferred substituents for aryl or heterocyclyl are halogen, cyano, thiophenyl, thiazolyl, oxazolyl or acetyl.

Very particular preference is therefore given, for example, to compounds of the general formulae (I), (Ia), (Ib), (Ic) and (Id) in which R is hydrogen or deuterium;

$R^1$ is formyl, acetyl, halogen, cyano or unsubstituted or mono-substituted furyl, pyrrolidinyl, thiophenyl, thiazolyl or oxazolyl; and $R^2$ is, independently of one another, hydrogen, halogen, cyano or $C_1$-$C_8$-alkyl.

Particularly preferred compounds of the formula (I) are those of the general formulae (Ia'-Id') having a specific configuration at the asymmetric carbon atom labelled "*"

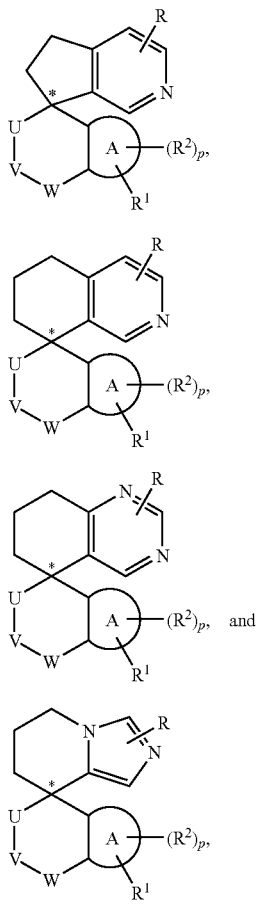

the definitions of the substituents A, R, R¹, R², U, V, W and p being as specified for the compounds of the formula (I).

The compounds of the formula (I) which possess at least one asymmetric carbon atom can exist in the form of optically pure enantiomers, mixtures of enantiomers, or racemates. Compounds having a second asymmetric carbon atom can exist in the form of optically pure diastereomers, mixtures of diastereomers, diastereomeric racemates, mixtures of diastereomeric racemates, or mesocompounds. The invention embraces all of these forms.

Mixtures of enantiomers, racemates, mixtures of diastereomers, diastereomeric racemates, or mixtures of diastereomeric racemates can be fractionated by conventional methods, such as by racemate resolution, column chromatography, thin-layer chromatography, HPLC and the like.

The compounds of the formula (Ia'-Id') have at least one asymmetric carbon atom, which is labelled "*". The compounds mentioned are to be understood as a single compound having a specific configuration around the designated asymmetric carbon atom. If a synthesis method is used which leads to racemic compounds, the racemate resolution is carried out in accordance with conventional methods, such as via a chiral HPLC column. Compounds of the formula (Ia'-Id') as described in the present invention exhibit a pronounced aldosterone synthase and/or 11-β-hydroxylase inhibitory activity. The aforementioned activity can, as the skilled worker is well aware and as described below, be comfortably determined via cellular assays based on the NCI-H295R human adrenocortical carcinoma cell line. In the above-mentioned assay system, compounds of the formula (Ia'-Id') have an activity which is at least 20 times better, but preferably 40 times better, than the substances of the formula (Ia'-Id') with the opposite configuration around the asymmetric carbon atom labelled "*".

The expression "pharmaceutically useful salts" embraces salts with organic or inorganic acids, such as hydrochloric acid, hydrobromic acid, nitric acid, sulphuric acid, phosphoric acid, citric acid, formic acid, maleic acid, acetic acid, succinic add, tartaric acid, methane-sulphonic acid, p-toluenesulphonic acid and the like. Salts of compounds containing salt-forming groups are, in particular, acid addition salts, salts with bases or else, if appropriate, if two or more salt-forming groups are present, are mixed salts or inner salts.

The compounds of the formula (I) can be prepared analogously to preparation processes known from the literature. Details of the specific preparation variants can be found from the examples.

The compounds of the formula (I) can also be prepared in optically pure form. Separation into antipodes is possible by methods known per se, either, preferably, at an early stage in synthesis, by salt formation with an optically active acid such as, for example, (+y or (−)-mandelic acid and separation of the diastereomeric salts by fractional crystallization, or, preferably, at a fairly late stage, by derivatization with a chiral auxiliary component, such as, for example, (+)- or (−)-camphanyl chloride and separation of the diastereomeric products by chromatography and/or crystallization and subsequent cleavage of the bond to the chiral auxiliary. The pure diastereomeric salts and derivatives can be analyzed to determine the absolute configuration of the compound present, using customary spectroscopic methods, with single-crystal X-ray spectroscopy representing one particularly appropriate method.

Salts are primarily the pharmaceutically useful or non-toxic salts of compounds of the formula (I). Such salts are formed for example by compounds of the formula (I) containing an acidic group, such as a carboxyl or sulpho group and are, for example, salts thereof with suitable bases, such as non-toxic metal salts derived from metals of group Ia, Ib, IIa and IIb of the Periodic Table of the Elements, such as alkali metal salts, especially lithium, sodium or potassium salts, alkaline earth metal salts, magnesium or calcium salts for example, and also zinc salts or ammonium salts, and additionally salts formed with organic amines, such as unsubstituted or hydroxyl-substituted mono-, di- or trialkylamines, especially mono-, di- or tri-lower alkylamines, or with quaternary ammonium bases, e.g. methyl-, ethyl-, diethyl- or triethylamine, mono-, bis- or tris(2-hydroxy-lower alkyl) amines, such as ethanolamine, diethanolamine or triethanolamine, tris(hydroxymethyl)methylamine or 2-hydroxy-tertiary-butylamine, N,N-di-lower alkyl-N-(hydroxy-lower alkyl)amine, such as N,N-di-N-dimethyl-N-(2-hydroxy-ethyl)amine, or N-methyl-D-glucamine, or quaternary ammonium hydroxides, such as tetrabutylammonium hydroxide. The compounds of the formula (I) containing a basic group, such as amino group, can form acid addition salts, with suitable inorganic acids for example, such as hydrohalic acid, such as hydrochloric acid, hydrobromic acid, or sulphuric acid with replacement of one or both protons, phosphoric acid with replacement of one or more protons, orthophosphoric acid or metaphosphoric acid for example, or pyrophosphoric acid with replacement of one or more protons, or with organic carboxylic, sulphonic or phosphonic acids or N-substituted sulphamic acids, examples being acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, such as α-amino acids, and also methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (to form cyclamates), or with other acidic organic compounds, such as ascorbic acid. Compounds of the formula (I) containing acidic and basic groups can also form inner salts.

Isolation and purification can also be carried out using pharmaceutically unsuitable salts.

The compounds of the formula (I) also include those compounds in which one or more atoms have been replaced by their stable, non-radioactive isotopes: for example, a hydrogen atom by deuterium.

Prodrug derivatives of the presently described compounds are derivatives thereof which when employed in vivo release the original compound as a result of a chemical or physiological process. A prodrug may be converted into the original compound, for example, when a physiological pH is reached or as a result of enzymatic conversion. Examples of possible prodrug derivatives include esters of freely available carboxylic acids, S- and O-acyl derivatives of thiols, alcohols or phenols, the acyl group being defined as above. Preference is given to pharmaceutically useful ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxyl, lower alkoxycarbonyl) alkyl esters or such as lower α-(alkanoyloxy, alkoxycarbonyl or dialkylaminocarbonyl)alkyl esters; pivaloyloxymethyl esters and similar esters are conventionally used as ester derivatives of this kind.

Because of the dose relationship between a free compound, a prodrug derivative and a salt compound, a defined compound in this invention also includes its prodrug derivative and salt form, insofar as this is possible and appropriate.

Aldosterone is a steroidal hormone which is synthesized in the zona glomerulosa cells of the adrenal cortex by the enzyme aldosterone synthase (CYP11B2). Aldosterone production and secretion is regulated by the adrenocorticotropic hormone (ACTH), angiotensin II, potassium and sodium ions. The primary biological function of aldosterone is the regulation of the salt balance, with aldosterone controlling the reabsorption of sodium ions from the renal filtrate and the secretion of potassium ions into the renal filtrate. The state of excessive aldosterone secretion, also called hyperaldosteronism, can lead to high blood pressure, hypokalaemia, alkalosis, muscle weakness, polyuria, polydipsia, edemas, vasculitis, increased collagen formation, fibrosis and endothelial dysfunction.

The chemical compounds described in this invention inhibit the cytochrome P450 enzyme aldosterone synthase (CYP11B2) and can therefore be used to treat states induced by aldosterone. The compounds described can be employed for preventing, delaying the progression of or treating states such as hypokalaemia, hypertension, congestive heart failure, acute and—in particular—chronic renal failure, cardiovascular restenosis, atherosclerosis, metabolic syndrome (syndrome X), adiposity (obesity), vasculitis, primary and secondary hyperaldosteronism, proteinuria, nephropathy, diabetic complications, such as diabetic nephropathy, myocardial infarction, coronary heart disease, increased collagen formation, fibrosis, vascular and coronary tissue changes (remodelling) secondary to high blood pressure, endothelial dysfunction, and oedemas secondary to sclerosis, nephrosis and congestive heart failure.

Cortisol is a steroidal hormone which is synthesized almost exclusively in the zona fasciculata cells of the adrenal cortex by the cytochrome P450 enzyme 11-β-hydroxylase (CYP11B1). Cortisol production is regulated by ACTH. The primary biological function of cortisol is to regulate the production and the provision of carbohydrates for the brain and other metabolically active tissues. Increased cortisol production and secretion is a normal physiological response to stress and leads to the essential mobilization of fats, proteins and carbohydrates to cover increased physical energy demand. Chronically excessive cortisol release describes the condition of Cushing's syndrome. Cushing's syndrome may come about on the one hand as a result of cortisol hypersynthesis, which may be generated by an adrenocortical tumour, or on the other hand as the consequence of excessive stimulation of the adrenal cortex by ACTH. The first form is referred to as primary hypercortisolism, the second form as secondary hypercortisolism. An excessive and persistent cortisol secretion may also accompany a stress response, which can lead to depression, hyperglycaemia and the suppression of the immune system.

The chemical compounds described in this invention inhibit the enzyme 11-β-hydroxylase (CYP11B1) and may therefore, owing to the inhibition of cortisol synthesis, be employed for preventing, delaying the progression of or treating Cushing's syndrome and also the physical and mental consequences of excessive and persistent cortisol secretion in states of stress. Consequently, moreover, the compounds can be employed in states such as ectopic ACTH syndrome, the change in adrenocortical mass, primary pigmented nodular adrenocortical disease (PPNAD) and Carney complex (CNC), anorexia nervosa, chronic alcohol poisoning, nicotine or cocaine withdrawal syndrome, post-traumatic stress syndrome, cognitive impairment after a stroke, and cortisol-induced mineralocorticoid excess.

Inhibition of aldosterone synthase (Cyp11B2) and of 11-β-hydroxylase (Cyp11B1) and of aromatase (Cyp19) by compounds described above can be determined by the following in vitro assay:

The cell line NCI-H295R was originally isolated from an adrenocortical carcinoma and has been characterized in the literature through the stimulable secretion of steroid hormones and the presence of the enzymes essential for steroidogenesis. Thus, the NCI-H295R cells have Cyp11A (cholesterol side-chain cleavage), Cyp11B1 (steroid 11β-hydroxylase), Cyp11B2 (aldosterone synthase), Cyp17 (steroid 17α-hydroxylase and/or 17,20-lyase), Cyp19 (aromatase), Cyp21B2 (steroid 21-hydroxylase) and 3β-HSD (hydroxysteroid dehydrogenase). The cells show the physiological property of zonally undifferentiated human foetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbecco's Modified Eagle'Ham F-12 Medium (DME/F12) which has been supplemented with Ultroser SF Serum (Soprachem, Cergy-Saint-Christophe, France), insulin, transferrin, selenite (I-T-S, Becton Dickinson Biosciences, Franklin Lakes, N.J., USA) and antibiotics in 75 $cm^2$ cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum albumin instead of Ultroser SF, for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin II (10 or 100 nanomolar), potassium ions (16 millimolar), forskolin (10 micromolar) or a combination of two stimulants. The excretion of aldosterone, cortisol, corticosterone and estradiol/estrone into the culture medium can be detected and quantified by commercially available, specific monoclonal antibodies in radioimmunoassays in accordance with the manufacturers' instructions. Inhibition of the release of certain steroids can be used as a measure of the respective enzyme inhibition by the added test compounds. The dose-dependent inhibition of enzymic activity by a compound is calculated by means of an inhibition plot which is characterized by an $IC_{50}$.

The $IC_{50}$ values for active test compounds are ascertained by a simple linear regression analysis in order to constrict inhibition plots without data weighting. The inhibition plot is calculated by fitting a 4-parameter logistic function to the raw data points using the least squares method. The equation of the 4-parameter logistic function is calculated as follows:

$$Y=(d-a)/((1+(x/c)^{-b}))+a$$

where:
a=minimum data level
b=gradient
c=$IC_{50}$
d=maximum data level
x=inhibitor concentration.

The compounds of the present invention show inhibitory effects at minimum concentrations of about $10^{-3}$ to about $10^{-10}$ mol/in the in vitro systems.

The aldosterone-reducing effect of the compounds described herein can be tested in vivo by the following protocol:

Adult male Sprague Dawley rats weighing between 125 and 150 grams are kept, housed individually, under the usual conditions of light and temperature. At 16.00 h on the first day of the experiment, the animals receive a subcutaneous injection of the depot ACTH product in a dose of 1.0 mg/kg of weight (SYNACTEN-Depot, Novartis, Basel, CH). Pilot studies showed that this ACTH dose increased plasma aldosterone and corticosterone significantly by respectively 15-fold and 25-fold over a period of at least 18 hours. At 8.00 h in the morning of the second day, the animals, divided into test groups of 5 animals, receive administration either of water orally or of a compound in a variable dose range of 0.01-10 mg/kg orally by gavage. Two hours later, blood is taken in EDTA-treated Eppendorf vessels. Plasma samples are obtained by centrifugation of the blood and can be stored at −20° C.

An alternative method for stimulating aldosterone synthesis is for adult male, catheterized Wistar rats, weighing between 250 and 350 grams, to be subjected to a low-salt diet for 48 hours and additionally be treated 16 hours, and possibly with additional repetition 2 hours, before the start of the experiment with 10 mg/kg furosemide, administered subcutaneously or intraperitoneally. Pilot studies showed that this pretreatment increases the plasma aldosterone level by 5 to 20-fold over a period of 12-24 hours. The catheters are chronically implanted into the animals' carotid and thus permit periodic blood sampling of a volume of up to 0.2 ml using an AccuSampler (DiLab Europe, Lund, Sweden). The experiment starts with the oral administration of the test substances in a dose range of 0.01-10 mg/kg. The blood samples are taken with the AccuSampler 1 hour before administration of the test substances and subsequently after 2, 4, 6, 8, 12, 16 and 24 hours. The blood samples are anticoagulated with heparin and centrifuged.

The plasma samples of both protocols are tested for the steroid content in precedingly described radioimmunoassays. The reduction in the steroid levels, such as, for example, aldosterone, serves as a measure of the in vivo bioavailability and enzyme inhibition activity of the compounds described herein.

The reduction in damage to the heart through the inhibition of aldosterone synthase with compounds described herein can be shown in vivo by the following protocol. The protocol corresponds in large part to the publication (Rocha et al, Endocrinology, Vol. 141, pp 3871-3878, 2000).

Adult male Wistar rats are housed individually and receive freely available drinking water which contains 0.9% sodium chloride during the experiment. Three days later, the animals are subjected to one of the three following treatments. Group I (control group of 8 animals) is treated for 14 days with the chemical L-NAME (N-nitro-L-arginine methyl ester, Sigma, St. Louis, Mo., USA) which inhibits nitric-oxide synthase. On day 11 of this treatment, an osmotic minipump charged with sodium chloride solution is subcutaneously implanted into each animal. Group II (L-NAME/AngII of 8 animals) is treated with L-NAME for 14 days. On day 11 of this treatment, an osmotic minipump charged with angiotensin II (AngII) solution is subcutaneously implanted into each animal. Group III (L-NAME/AngII/test substance of 8 animals) is treated similarly to group II but receives the test substance in a daily dose range from 0.2 to 10 mg/kg of rat weight. The test substance is for this purpose dissolved in distilled water and administered orally by gavage. Groups I and II receive only the vehicle without test substance. The experiment is stopped on day 14 of L-NAME treatment. L-NAME is administered in a concentration of 60 mg/100 mL in the 0.9% NaCl drinking water, leading to a daily intake of about 60 mg/kg. Angiotensin II is administered by means of an Alzet osmotic minipump (model 2001; Alza Corp, Palo Alto, Calif.). The minipump is implanted subcutaneously in the back of the neck. Angiotensin II (human and with a peptide purity of 99%) is purchased from Sigma Chemical Co., St. Louis, Mo. and administered in a dose of 225 µg/kg/day in sodium chloride solution. The concentration of angiotensin II for charging the pumps is calculated on the basis of: a) the average pumping rate stated by the manufacturer; b) the body weight of the animals on the day before implantation of the pumps; and c) the planned dose.

The rats are sacrificed on day 14. The hearts are removed and the ventricles/atria are sliced like a "loaf of bread" in order to obtain three samples from the following approximate regions of the heart: superior, middle and inferior. The samples are fixed in 10% buffered formalin. Paraffin sections are cut and stained with hematoxylin/eosin. The sections are assessed by a single scientist unaware of the assignment to groups. One section from each region of the heart is analyzed for each rat. Specific parts of the heart (left and right ventricle, and the septum) are evaluated separately. The whole section is examined histologically for myocardial damage (irrespective of severity) manifested by myocyte necrosis, inflammatory cells, hemorrhages and general tissue damage. The histological data are assessed on the basis of a comparison of groups II and III, i.e. angiotensin II with and without test substance.

Evaluation of the samples can take place semiquantitatively and be represented in the form of a point table.

The reduction in hypertension and the diminution in damage to the heart and kidneys through inhibition of aldosterone synthase with compounds described herein can be shown in vivo by the following protocol.

The investigations take place in 4-week old, male doubly transgenic rats (dTGR), which over-express both human angiotensinogen and human renin and consequently develop hypertension. Age-matched Sprague-Dawley (SD) rats serve as non-hypertensive control animals. The animals are divided into treatment groups and receive test substance or vehicle (control) each day for 3-4 weeks. Throughout the study, the animals receive standard feed and tap water ad libitum.

The systolic and diastolic blood pressure, and the heart rate, are measured telemetrically by means of implanted transducers, allowing the animals free and unrestricted movement. The animals are placed once a week in metabolism cages in order to determine the 24-hour urinary excretion of albumin. Heart dimensions (left ventricular mass, end-diastolic diameter and wall thickness, septum thickness, shortening fraction) and diastolic filling are measured by echocardiography at the start and at the end of the treatment under isoflurane anesthesia (M mode recording in the short axis and tissue Doppler imaging by means of a commercial echocardiography instrument which is equipped with a 15 MHz probe). At the end of the study, the animals are sacrificed and the kidneys and hearts are removed for determining the weight and for immunohistological investigations (fibrosis, macrophage/T cell infiltration, etc.).

In order to achieve the desired effects in a patient to be treated, the compounds of the present invention can be administered orally or enterally, such as, for example, intravenously, intraperitoneally, intramuscularly, rectally, subcutaneously or else by direct injection of the active substance locally into tissues or tumours. The term patient encompasses warm-blooded species and mammals such as, for example, human, primate, bovine, dog, cat, horse, sheep, mouse, rat and pig. The compounds can be administered as pharmaceutical product or be incorporated into an administration device which ensures sustained release of the compound. The amount of substance to be administered can vary over a wide range and represent every effective dose. Depending on the patient to be treated or the condition to be treated and mode of administration, the dose of the effective substance each day can be between about 0.005 and 50 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatin capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatin, disintegrants such as potato starch or crosslinked polyvinylpyrrolidone (PVPP) and lubricants such as stearic acid or magnesium stearate.

Examples of excipients suitable for soft gelatin capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semiliquid or liquid polyols etc.

For parenteral administration, the compounds can be formulated as injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as transdermal patch system, as depot injection or implant if the formulation makes sustained delivery of the active ingredient possible. The active substance can be compressed as granules or to narrow cylinders and be administered subcutaneously or intramuscularly as depot injection or implant.

The pharmaceutical products may in addition also comprise preservatives, solubilizers, viscosity-increasing substances, stabilizers, wetting agents, emulsifiers, sweeteners, colorants, aromatizing agents, salts to change the osmotic pressure, buffers, coating agents or antioxidants. They may also comprise other therapeutically valuable substances too.

The compounds of the invention described herein permit the following methods of use:

as therapeutic combination in the form of a product or of a kit which is composed of individual components consisting of a compound described herein, in free form or as pharmaceutically useful salt, and at least one pharmaceutical form whose active ingredient has a blood pressure-lowering, an inotropic, an antidiabetic, an obesity-reducing or a lipid-lowering effect, which can be used either simultaneously or sequentially. The product and the kit may comprise instructions for use.

as method for combined use, such as, for example, in simultaneous or sequential succession, of a therapeutically effective amount of a compound described herein, in free or in pharmaceutically useful salt form, and of a second active ingredient with blood pressure-lowering, inotropic, antidiabetic, obesity-reducing or lipid-lowering effect.

The compounds described herein and their pharmaceutically useful salts can be used in combination with (i) one or more blood pressure-lowering active ingredients, as such for example:

renin inhibitors such as aliskiren;

angiotensin II receptor blockers such as candesartan, irbesartan, olmesartan, losartan, valsartan, telmisartan etc.;

ACE inhibitors such as quinapril, ramipril, trandolapril, lisinopril, captopril, enalapril etc.;

calcium antagonists such as nifedipine, nicardipine, verapamil, isradipine, nimodipine, amlodipine, felodipine, nisoldipine, diltiazem, fendiline, flunarizine, perhexyline, gallopamil etc.;

diuretics such as hydrochlorothiazide, chlorothiazide, acetazolamide, amiloride, bumetanide, benzthiazide, etacrynic acid, furosemide, indacrinone, metolazone, triamterene, chlortalidone, etc.;

aldosterone receptor blockers such as spironolactone, eplerenone;
endothelin receptor blockers such as bosentan;
phosphodiesterase inhibitors such as amrinone, sildenafil;
direct vasodilators such as dihydralazine, minoxidil, pinacidil, diazoxide, nitroprusside, flosequinan etc.,
α- and β-receptor blockers such as phentolamine, phenoxybenzamine, prazosin, doxazosin, terazosin, carvedilol, atenolol, metoprolol, nadolol, propranolol, timolol, carteolol etc.;
neutral endopeptidase (NEP) inhibitors;
sympatholytics such as methyldopa, clonidine, guanabenz, reserpine
(ii) one or more agents having inotropic activity, as such for example:
cardiac glycosides such as digoxin;
β-receptor stimulators such as dobutamine
thyroid hormone such as thyroxine
(iii) one or more agents having antidiabetic activity, as such for example:
insulins such as insulin aspart, insulin human, insulin lispro, insulin glargine and further fast-, medium- and long-acting insulin derivatives and combinations
insulin sensitizers such as rosiglitazone, pioglitazone;
sulphonylureas such as glimepiride, chlorpropamide, glipizide, glyburide etc.;
biguanides such as metformin;
glucosidase inhibitors such as acarbose, miglitol;
meglitinides such as repaglinide, nateglinide;
(iv) one or more obesity-reducing ingredients, as such for example:
lipase inhibitors such as orlistat;
appetite suppressants such as sibutramine, phentermine;
(v) one or more lipid-lowering ingredients, such as, for example,
HMG-CoA reductase inhibitors such as lovastatin, fluvastatin, pravastatin, atorvastatin, simvastatin, rosuvastatin etc.;
fibrate derivatives such as fenofibrate, gemfibrozil etc.;
bile acid-binding active ingredients such as colestipol, colestyramine, colesevelam
cholesterol absorption inhibitors such as ezetimibe
nicotinic acid such as niacin
and other agents which are suitable for the treatment of high blood pressure, heart failure or vascular disorders associated with diabetes and renal disorders, such as acute or chronic renal failure, in humans and animals. Such combinations can be used separately or in products which comprise a plurality of components.

The compounds described herein and their pharmaceutically useful salts can additionally be used in combination with
(i) a diagnostic test system which permits quantitative determination of the plasma aldosterone level (PAC, plasma aldosterone concentration)
(ii) a diagnostic test system which permits quantitative determination of the plasma renin level (PRC, plasma renin concentration)
(iii) a diagnostic test system which permits quantitative determination of the plasma renin activity (PRA, plasma renin activity)
(iv) a diagnostic test system which permits quantitative determination of the plasma aldosterone/renin level (ARC, aldosterone renin concentration)
(v) a diagnostic test system which permits quantitative determination of the plasma aldosterone/renin activity (ARR, aldosterone to renin activity ratio)
(vi) a diagnostic test system which permits quantitative determination of the plasma cortisol level (PCC, plasma cortisol concentration)

Such diagnosis-therapy combinations can be used separately or in products which comprise a plurality of components.

EXAMPLES

The following examples illustrate the present invention. All temperatures are stated in degrees Celsius, pressures in mbar. Unless mentioned otherwise, the reactions take place at room temperature. The abbreviation "Rf=xx(A)" means for example that the Rf is found in solvent system A to have the value xx. The proportion of solvents to one another is always stated in fractions by volume. Chemical names of end products and intermediates were generated with the aid of the AutoNom 2000 (Automatic Nomenclature) program. Chemical names of spiro-compounds were generated with the aid of the ACD-Name program.

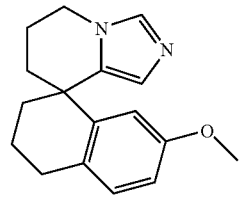

1

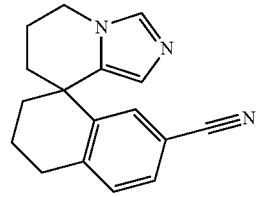

2

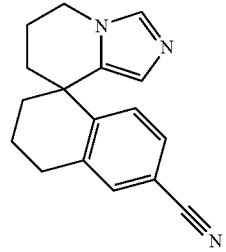

3

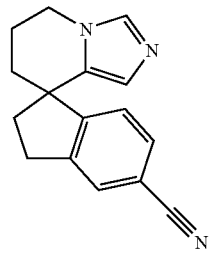

4

-continued
5
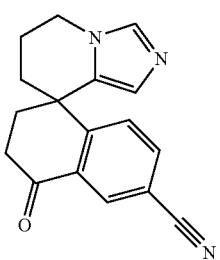
6
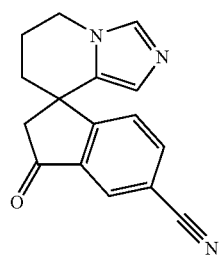
7
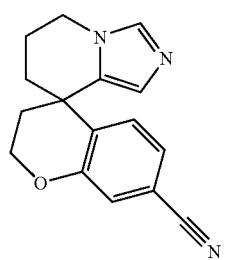
8
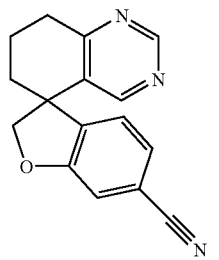
9
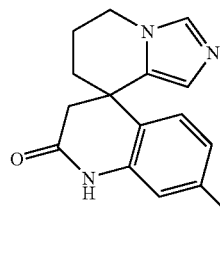
10
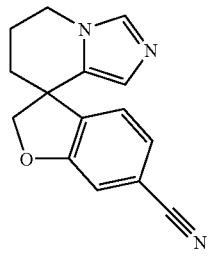
-continued
11
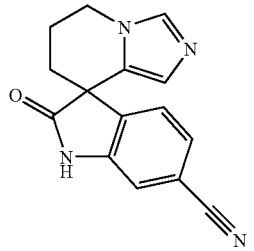
12
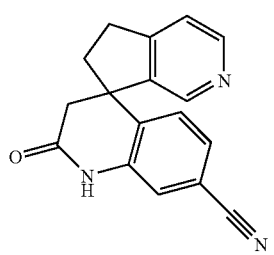
13
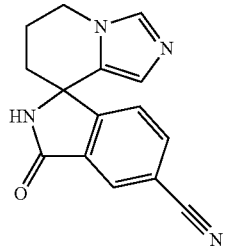
14
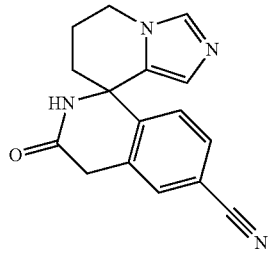
15
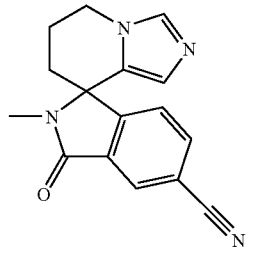
16
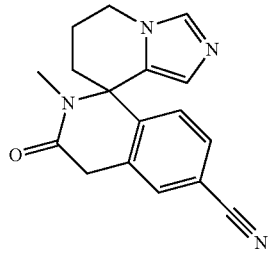

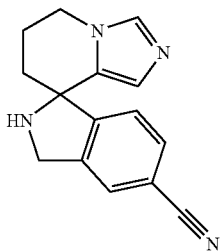

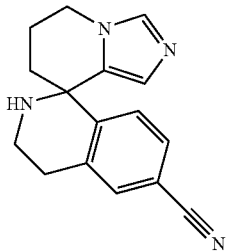

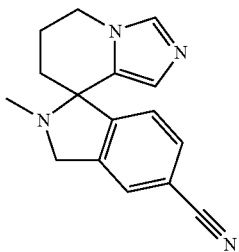

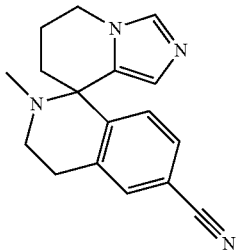

Thin-layer chromatography mobile-phase systems:
A Dichloromethane
B Dichloromethane-methanol=99:1
C Dichloromethane-methanol=98:2
D Dichloromethane-methanol=97:3
E Dichloromethane-methanol=96:4
F Dichloromethane-methanol=95:5
G Dichloromethane-methanol=9:1
H Dichloromethane-methanol=4:1
I Dichloromethane-methanol-water-conc. acetic acid=170:26:3:1
J Dichloromethane-methanol-water-conc. acetic acid=150:54:10:1
K Dichloromethane-methanol-conc. ammonia 25%=97:3:1
L Dichloromethane-methanol-conc. ammonia 25%=95:5:1
M Dichloromethane-methanol-conc. ammonia 25%=90:10:1
N Dichloromethane-methanol-conc. ammonia 25%=200:10:1
O Dichloromethane-methanol-conc. ammonia 25%=200:20:1
P Ethyl acetate
Q Ethyl acetate-heptane=3:1
R Ethyl acetate-heptane=2:1
S Ethyl acetate-heptane=1:1
T Ethyl acetate-heptane=1:2
U Ethyl acetate-heptane=1:3
V Ethyl acetate-heptane=1:4
W Ethyl acetate-heptane=1:5
X Ethyl acetate-heptane=1:6
Y Ethyl acetate-heptane=1:10
Z Toluene/ethyl acetate=1:1
AA Toluene/methanol=6:1

HPLC gradients on Hypersil BDS C-18 (5 µm); column: 4×125 mm:
95% water*/5% acetonitrile* to 0% water*/100% acetonitrile* in 10 minutes+2 minutes (1 ml/min)
* contains 0.1% trifluoroacetic acid The abbreviations used are as follows:
Rf ratio of distance traveled by a substance to distance of the eluent from the starting point in thin-layer chromatography
Rt retention time of a substance in HPLC (in minutes)
m.p. melting point (temperature)

Example 1

7'-Methoxy-3',4',6,7-tetrahydro-2'H,5H-spiro[imidazo[1,5-a]pyridine-8,1'-naphthalene]

A mixture of 10.500 mmol of 8-[3-(4-methoxyphenyl)propyl]-5,6,7,8-tetrahydroimidazo-[1,5-a]pyridin-81 in 50 ml of dichloromethane and 15 g of polyphosphoric acid is reacted in an ultrasound bath for 5 hours. The reaction mixture is diluted with 50 ml of ice-water and adjusted to a pH of 8 using 5M NaOH. The organic phase is separated off and the aqueous phase is extracted with dichloromethane (3×). The combined organic phases are dried with sodium sulphate and evaporated. The title compound is obtained as a yellow oil. The crude title compound is reacted further without further purification. Rf=0.32 (dichloromethane-ethanol=95:5); Rt=5.98.

The starting material is prepared as follows:

a) 8-[3-(4-Methoxyphenyl)propyl]-5,6,7,8-tetrahydroimidazo[1,5-a]pyridin-8-ol

A three-necked flask with dropping funnel and reflux condenser is charged with 285.000 mmol of magnesium turnings in 50 ml of THF. With stirring at an oil bath temperature of 70° C. a solution of 37.100 mmol of 3-(4-methoxyphenyl)bromopropane [57293-19-3] and 28.500 mmol 1-bromo-2-chloroethane in 40 ml of THF is added dropwise over 45 minutes. The mixture is subsequently stirred at 70° C. for 2 hours and then cooled to room temperature and the supernatant solution is transferred using a transfer cannula into a second three-necked flask, fitted with dropping funnel. The Grignard solution thus obtained is admixed dropwise, with ice-bath cooling, with 28.500 mmol of 6,7-dihydro-5H-imidazo[1,5-a]pyridin-8-one [426219-51-4] in solution in 50 ml of THF over 10 minutes. When addition is complete the reaction mixture is stirred at room temperature for 1 hour. It is quenched with 150 ml of 0.5M aqueous HCl and extracted with dichloromethane (3×). The combined organic phases are dried over sodium sulphate and evaporated. From the residue the title compound is obtained by means of flash chromatography (SiO₂ 60F) as an amber oil. Rf=0.08 (dichloromethane-ethanol=98:2); Rt=5.50.

Example 2

3',4',6,7-Tetrahydro-2'H,5H-spiro[imidazo[1,5-a]pyridine-8,1'-naphthalene]-7'-carbonitrile An apparatus purified by baking is charged under argon with 1.160 mmol of 3',4',6,7-tetrahydro-2'H,5H-spiro[imidazo[1,5-a]pyridine-8,1'-naphthalen]-7'-yl trifluoromethanesulphonate together with 2.320 mmol zinc(II) cyanide in 15 ml of degassed N,N-dimethylformamide. 0.093 mmol of tetrakis(triphenylphosphine)palladium is added and the reaction mixture is stirred at 120° C. for 20 hours. The reaction mixture is cooled and poured into 100 ml of ice-water. It is extracted with ethyl acetate (3×). The combined organic phases are dried over magnesium sulphate and evaporated. From the residue the title compound is obtained by means of flash chromatography (SiO$_2$ 60F) as a white solid. Rf=0.165 (dichloromethane-2M ammonia in EtOH=95:5); Rt=5.64.

The starting materials are prepared as follows:

a) 3',4',6,7-Tetrahydro-2'H,5H-spiro[imidazo[1,5-a]pyridine-8,1'-naphthalen]-7'-yl trifluoromethanesulphonate 3.930 mmol of 3',4',6,7-tetrahydro-2'H,5H-spiro[imidazo[1,5-a]pyridine-8,1'-naphthalen]-7'-ol, 7.86 mmol pf N-ethyldiisopropylamine and 7.860 mmol of N-phenylbis(trifluoromethanesulphonimide) are stirred in 25 ml of dichloromethane at room temperature for 20 hours. The reaction mixture is evaporated and from the residue the title compound is obtained by means of flash chromatography (SiO$_2$ 60F) as a yellow oil. Rf=0.25 (dichloromethane-2M ammonia in EtOH=95:5); Rt=7.00.

b) 3',4',6,7-Tetrahydro-2'H,5H-spiro[imidazo[1,5-a]pyridine-8,1'-naphthalen]-7'-ol 7.450 mmol of 7'-methoxy-3',4',6,7-tetrahydro-2'H,5H-spiro[imidazo[1,5-a]pyridine-8,1'-naphthalene] (Example 1) are introduced at 0° C. into 50 ml of dichloromethane. 18.630 mmol of boron tribromide (1M in dichloromethane) are added dropwise over 20 minutes. The reaction mixture is subsequently stirred at 0° C. for 3 hours. It is admixed with 50 ml of saturated aqueous sodium bicarbonate solution and stirred thoroughly for 30 minutes. The organic phase is separated off and the aqueous phase is extracted with 30 ml of dichloromethane. The combined organic phases are dried with magnesium sulphate and evaporated. The title compound is obtained as a yellow foam. The crude title compound is reacted further without further purification. Rf=0.28 (dichlormethane-ethanol=95:5); Rt=5.22.

The compounds below are prepared by methods analogous to those described in Examples 1 and 2:

3 3',4',6,7-Tetrahydro-2'H,5H-spiro[imidazo[1,5-a]pyridine-8,1'-naphthalene]-6-carbonitrile starting from 3-(3-methoxyphenyl)bromopropane [6943-97-1]

4 2',3',6,7-Tetrahydro-5H-spiro[imidazo[1,5-a]pyridine-8,1'-indene]-5'-carbonitrile The title compound is obtained by a method analogous to that described in Example 2, 2a and 2b, starting from 5'-methoxy-2',3',6,7-tetrahydro-5H-spiro[imidazo[1,5-a]pyridine-8,1'-indene] and identified on the basis of the Rf value.

The starting material is prepared as follows:

a) 5'-Methoxy-2',3',6,7-tetrahydro-5H-spiro[imidazo[1,5-a]pyridine-8,1'-indene]

The title compound is obtained by a method analogous to that described in Example 1 and 1a, starting from 3-(3-methoxyphenyl)bromoethane [2146-61-4] and identified on the basis of the Rf value.

Example 5

4'-Oxo-3',4',6,7-tetrahydro-2'H,5H-spiro[imidazo[1,5-a]pyridine-8,1'-naphthalene]-6'-carbonitrile The title compound is obtained by a method analogous to that described in Example 2, 2a and 2b, from 6'-methoxy-2',3',6,7-tetrahydro-4'H,5H-spiro[imidazo[1,5-a]pyridine-8,1'-naphthalen]-4'-one and identified on the basis of the Rf value.

The starting material is prepared as follows:

a) 6'-Methoxy-2',3',6,7-tetrahydro-4'H,5H-spiro[imidazo[1,5-a]pyridine-8,1'-naphthalen]-4'-One A solution of 1 mmol of 7'-methoxy-3',4',6,7-tetrahydro-2'H,5H-spiro[imidazo[1,5-a]pyridine-8,1'-naphthalene] (Example 1) in 20 ml of dimethylsulphoxide is admixed with 3 mmol of 1-hydroxy-3H-benz[d][1,2]iodooxole-1,3-dione (IBX) [61717-82-6] and the mixture is heated at 90° C. for 2 hours. It is cooled to room temperature and diluted with diethyl ether. The organic phase is washed with 5% sodium hydrogen carbonate (3×) and water, dried with magnesium sulphate and evaporated. From the residue the title compound is identified by means of flash chromatography (SiO$_2$ 60F) on the basis of the Rf value.

The compound below is prepared by a method analogous to that described in Example 5:

6 3'-Oxo-2',3',7,8-tetrahydro-6H-spiro[imidazo[1,5a]pyridine-5,1'-indene]-5'-carbonitrile The title compound is obtained by a method analogous to that described in Example 2, 2a and 2b, starting from 5'-methoxy-7,8-dihydro-6H-spiro[imidazo[1,5-a]pyridine-5,1'-inden]-3'(2'H)-one and identified on the basis of the Rf value.

The starting material is prepared as follows:

a) 5'-Methoxy-7,8-dihydro-6H-spiro[imidazo[1,5-a]pyridine-5,1'-inden]-3'(2'H)-one The title compound is obtained by a method analogous to that described in Example 5a, starting from 5'-methoxy-2',3',6,7-tetrahydro-5H-spiro[imidazo[1,5-a]pyridine-8,1'-indene] (Example 4a) and identified on the basis of the Rf value.

Example 7

2,3,6',7'-Tetrahydro-5'H-spiro[chromene-4,8'-imidazo[1,5-a]pyridine]-7-carbonitrile The title compound is obtained by a method analogous to that described in Example 2 and 2a, starting from 2,3,6',7'-tetrahydro-5'H-spiro[chromene-4,8'-imidazo[1,5-a]pyridin]-7-ol and identified on the basis of the Rf value.

The starting materials are prepared as follows:

a) 2,3,6',7'-Tetrahydro-5'H-spiro[chromene-4,8'-imidazo[1,5-a]pyridin]-7-ol

A mixture of 1 mmol of 7-methoxy-2,3,6',7'-tetrahydro-5'H-spiro[chromene-4,8'-imidazo[1,5-a]pyridine] and 5 ml of trimethylsilyl iodide in 20 ml of acetonitrile is heated at reflux for 24 hours. 5 ml of methanol are added cautiously and the mixture is heated at reflux for a further 30 minutes. The reaction mixture is evaporated. From the residue the title compound is identified by means of flash chromatography ($SiO_2$ 60F) on the basis of the Rf value.

b) 7-Methoxy-2,3,6',7'-tetrahydro-5'H-spiro[chromene-4,8'-imidazo[1,5-a]pyridine]

A solution of 2.61 mmol of trimethylsilyloxy trifluoromethanesulphonate in 1 ml of dichloro-methane at 0° C. is admixed with a solution of 1.27 mmol of titanium tetrachloride in 1.5 ml of dichloromethane. The mixture is stirred at room temperature for 4 hours and then cooled to 0° C. A solution of 0.83 mmol of 7-methoxy-6',7'-dihydro-5'H-spiro[chromene-4,8'-imidazo[1,5-a]pyridin]-2(3H)-one and 4.17 mmol of triethylsilane in 2 ml of dichloromethane is added and the reaction mixture is stirred at room temperature for 20 hours. The reaction mixture is poured into ice-water and extracted with ethyl acetate (2×). The combined organic phases are washed with water and brine, dried with sodium sulphate and evaporated. From the residue the title compound is identified by means of flash chromatography ($SiO_2$ 60F) on the basis of the Rf value.

c) 7-Methoxy-6',7'-dihydro-5'H-spiro[chromene-4,8'-imidazo[1,5-a]pyridin]-2(3H)-one A solution of 1.20 mmol of 4-(3-hydroxypropyl)-4-(1H-imidazol-4-yl)-7-methoxychroman-2-one and 1.44 mmol of N-ethyldiisopropylamine in 10 ml of dichloromethane is admixed dropwise at room temperature with 1.20 mmol of methanesulphonyl chloride and the reaction mixture is subsequently stirred for 3 hours. The conversion to the mesylate intermediate is observed by means of HPLC. The reaction mixture is poured into 10 ml of water and subjected to extraction and the aqueous phase is re-extracted with dichloromethane (2×). The combined organic phases are washed with brine, dried over sodium sulphate and evaporated (bath temperature: 30° C.). The residue is taken up in 10 ml of acetonitrile and heated at boiling on an oil bath for about 20 hours. The reaction mixture is left to cool and then evaporated. From the residue the title compound is identified by means of flash chromatography ($SiO_2$ 60F) on the basis of the Rf value.

d) 4-(3-Hydroxypropyl)-4-(1H-imidazol-4-yl)-7-methoxychroman-2-one

A solution of 1 mmol of 4-(1-benzyl-1H-imidazol-4-yl)-4-(3-benzyloxypropyl)-7-methoxychroman-2-one in 15 ml of methanol and 2 ml of conc HCl is hydrogenated in the presence of 100 mg of 10% Pd/C at 15° C. for 10 hours. The reaction mixture is subjected to clarifying filtration and the filtrate is evaporated. The crude title compound is identified on the basis of the Rf value and reacted further without further purification.

e) 4-(1-Benzyl-1H-imidazol-4-yl)-4-(3-benzyloxypropyl)-7-methoxychroman-2-one A solution of 1 mmol of 4-(1-benzyl-1H-imidazol-4-yl)-7-methoxychromen-2-one in 5 ml of tetrahydrofuran is added to a solution of 3 mmol of 3-(phenylmethoxy)propylmagnesium bromide [183312-54-1] in 5 ml of tetrahydrofuran. The mixture is subsequently stirred for 1 hour and then poured into saturated aqueous ammonium chloride solution. It is extracted with diethyl ether (3×). The combined organic phases are dried over sodium sulphate and evaporated. From the residue the title compound is identified by means of flash chromatography ($SiO_2$ 60F) on the basis of the Rf value.

f) 4-(1-Benzyl-1H-imidazol-4-yl)-7-methoxychromen-2-one

A mixture of 1 mmol of ethyl 3-(1-benzyl-1H-imidazol-4-yl)-3-oxopropionate and 1 mmol of 3-methoxyphenol [150-19-6] is admixed dropwise at 0° C. with 0.5 ml of concentrated sulphuric acid. 0.25 ml of phosphoryl chloride is added and the reaction mixture is stirred at room temperature for 17 hours. It is poured into a 1:1 mixture of ice and saturated, aqueous sodium hydrogen carbonate solution and extracted with chloroform (3×). The combined organic phases are dried over sodium sulphate and evaporated. From the residue the title compound is identified by means of flash chromatography ($SiO_2$ 60F) on the basis of the Rf value.

g) Ethyl 3-(1-benzyl-1H-imidazol-4-yl)-3-oxopropionate

A solution of 1 mmol of methyl 1-benzyl-1H-imidazole-4-arboxylate [74294-73-8] in 5 ml of toluene at 85° C. is admixed with 2 mmol of sodium hydride (60% dispersion in oil). 2 mmol of ethyl acetate are added dropwise over 2 hours and the mixture is stirred at 70° C. for 9 hours. The reaction mixture is evaporated. The crude title compound is identified on the basis of the Rf value and reacted further without further purification.

Example 8

7',8'-Dihydro-6'H-spiro[1-benzofuran-3,5'-quinazoline]-6-carbonitrile

The title compound is obtained by a method analogous to that described in Example 2 and 2a, starting from 7',8'-dihydro-6'H-spiro[1-benzofuran-3,5'-quinazolin]-6-ol and identified on the basis of the Rf value.

The starting materials are prepared as follows:

a) 7',8'-Dihydro-6'H-spiro[1-benzofuran-3,5'-quinazoline]-6-ol

The title compound is obtained by a method analogous to that described in Example 7b, starting from 6-methoxy-7',8'-dihydro-6'H-spiro[1-benzofuran-3,5'-quinazoline] and identified on the basis of the Rf value.

b) 6-Methoxy-7',8'-dihydro-6'H-spiro[1-benzofuran-3,5'-quinazoline]

A solution of 1 mmol of 5-(2-bromo-5-methoxyphenoxymethyl)-7,8-dihydroquinazoline, 0.5 mmol of azoisobutyronitrile (AIBN) and 1.5 mmol of tributyltin hydride in 50 ml of benzene is heated at reflux for 1-2 hours. The reaction solution is concentrated and the residue is taken up in diethyl ether. The solution is admixed with 1M NaOH and stirred vigorously at room temperature for 1 hour. The phases are separated and the organic phase is washed with 1M sodium hydroxide solution and brine, dried with sodium sulphate and evaporated. From the residue the title compound is identified by means of flash chromatography (SiO$_2$ 60F) on the basis of the Rf value.

c) 5-(2-Bromo-5-methoxyphenoxymethyl)-7,8-dihydroquinazoline

A solution of 10 mmol of 5-(2-bromo-5-methoxyphenoxymethyl)-5,6,7,8-tetrahydroquinazolin-5-ol and 20 mmol of phosphorus oxychloride in 20 ml of pyridine is heated at reflux for 0.5-1 hour. The mixture is poured onto ice and extracted with tert-butyl methyl ether. The combined organic extracts are washed with brine, dried with sodium sulphate and evaporated. From the residue the title compound is identified by means of flash chromatography (SiO$_2$ 60F) on the bias of the Rf value.

d) 5-(2-Bromo-5-methoxyphenoxymethyl)-5,6,7,8-tetrahydroquinazolin-5-ol

A solution of 10 mmol of 7',8'-dihydro-6'H-spiro[oxirane-2,5'-quinazoline] and 15 mmol of 2-bromo-5-methoxyphenol [63604-94-4] in 30 ml of 2-propanol is admixed with 20 mmol of finely powdered potassium carbonate. The mixture is heated at reflux for 12-18 hours, cooled and filtered over Hyflo. The filtrate is evaporated and from the residue the title compound is identified by means of flash chromatography (SiO$_2$ 60F) on the basis of the Rf value.

e) 7',8'-Dihydro-6'H-spiro[oxirane-2,5'-quinazoline]

Sodium hydride (22 mmol) washed with pentane is admixed under argon with 20 ml of dimethyl sulphoxide. The mixture is heated at 60° C. for an hour and then diluted with 5 ml of tetrahydrofuran. The mixture is cooled to 0° C., a solution of 21 mmol of trimethylsulphonium iodide in 5 ml of N,N-dimethylformamide is added at 0° C., and the mixture is stirred for 10 minutes. A solution of 20 mmol of 7,8-dihydro-6H-quinazolin-5-one [21599-28-0] in 5 ml of N,N-dimethylformamide is added and the reaction mixture is stirred at 20-60° C. for 18 hours. The reaction mixture is poured into cold brine and extracted with tert-butyl methyl ether. The combined organic phases are washed with brine, dried with sodium sulphate and evaporated. From the residue the title compound is identified by means of flash chromatography (SiO$_2$ 60F) on the basis of the Rf value.

The compound below is prepared by a method analogous to that described in Example 8:

10 6',7'-Dihydro-5'H-spiro[1-benzofuran-3,8'-imidazo[1,5-a]pyridine]-6-carbonitrile starting from 6,7-dihydro-5H-imidazo[1,5-a]pyridine-8-one [426219-51-4].

Alternative synthesis for 6',7'-dihydro-5'H-spiro[1-benzofuran-3,8'-imidazo[1,5-a]pyridine]-6-carbonitrile.

6',7'-Dihydro-5'H-spiro[1-benzofuran-3,8'-imidazo[1,5-a]pyridine]6-carbonitrile

The title compound is obtained by a method analogous to that described in Example 2, 2a and 2b, starting from 6-methoxy-6',7'-dihydro-5'H-spiro[1-benzofuran-3,8'-imidazo[1,5-a]pyridine] and identified on the basis of the Rf value. The starting materials are prepared as follows:

a) 6-Methoxy-6',7'-dihydro-5'H-spiro[1-benzofuran-3,8'-imidazo[1,5-a]pyridine]

A mixture of 1.9 mmol of 6-methoxy-1',6',7',8a'-tetrahydro-5'H-spiro[1-benzofuran-3,8'-imidazo[1,5-a]pyridine] and 3 g of manganese-dioxide in 50 ml of toluene is heated to reflux for 1.5 hours. The reaction mixture is cooled to room temperature, the solid is removed by filtration over Hyflo and the filtrate is evaporated. From the residue the title compound is identified by means of flash chromatography (SiO$_2$ 60F) on the basis of the Rf value.

b) 6-Methoxy-1',6',7',8a'-tetrahydro-5'H-spiro[1-benzofuran-3,8'-imidazo[1,5-a]pyridine]

A solution of 31 mmol of 1-(6-methoxyspiro[1-benzofuran-3,3'-piperidin]-2'-yl)methanamine and 31 mmol of N,N-dimethyl formamide dimethylacetal in 50 ml of dichloromethane is heated to reflux for 6 hours. The reaction mixture is cooled to room temperature and evaporated. The crude title compound is identified on the basis of the Rf value and reacted further without further purification.

c) 1-(6-Methoxyspiro[1-benzofuran-3,3'-piperidin]-2'-yl)methanamine

A mixture of 1 mmol of 1'-benzyl-6-methoxyspiro[1-benzofuran-3,3'-piperidine]-2'-carbonitrile and 50 mg of Raney-Nickel (activated by washing with water till pH 7 and washing with ethanol) in 5 ml of ethanol is hydrogenated for 12 hours under 500 psi hydrogen. The reaction mixture is filtered over Hyflo and the filtrate is evaporated. From the residue the title compound is identified by means of flash chromatography (SiO$_2$ 60F) on the basis of the Rf value.

d) 1'-Benzyl-6-methoxyspiro[1-benzofuran-3,3'-piperidine]-2'-carbonitrile

A solution of 8 mmol of lithium aluminum hydride (1M in hexane) in 40 ml of tetrahydrofuran at 0° C. is treated with 0.39 ml of ethyl acetate and stirred 2 hours at 0° C. To this solution, a solution of 1 mmol of 1'-benzyl-6-methoxy-2'H-spiro[1-benzofuran-3,3'-piperidin]-2'-one in 12.5 ml of tetrahydrofuran is added and the reaction mixture is stirred für 45 minutes at 0° C. 30 ml of acetic acid and 6 mmol of a 4.5M aqueous potassium cyanide solution are added consecutively. The reaction mixture is stirred for 16 hours at room temperature. The reaction mixture is diluted with 1M sodium bicarbonate solution and extracted with a 1:1 mixture of ethyl acetate-tetrahydrofuran (3×). The combined organic phases are washed with brine, dried with sodium sulphate and evaporated. From the residue the title compound is identified by means of flash chromatography (SiO$_2$ 60F) on the basis of the Rf value.

e) 1'-Benzyl-6-methoxy-2'H-spiro[1-benzofuran-3, 3'-piperidin]-2'-one

A suspension of 1 mmol of 1'-benzyl-6-hydroxy-2'H-spiro[1-benzofuran-3,3'-piperidin]-2'-one and 1.4 mmol of potassium carbonate in 7 ml of acetone are treated drop wise with 1.1 mmol of dimethyl sulfate. The reaction mixture is heated to reflux for 8 hours and then cooled to room temperature. The mixture is diluted with diethyl ether and 2M NaOH, the phases are separated and the organic phase is washed with brine, dried with sodium sulphate and evaporated. From the residue the title compound is identified by means of flash chromatography (SiO$_2$ 60F) on the basis of the Rf value.

f) 1'-Benzyl-6-hydroxy-2'H-spiro[1-benzofuran-3,3'-piperidin]-2'-one

A solution of 1 mmol of 1-benzyl-3-(2,4-dihydroxy-phenyl)-3-hydroxymethyl-piperidin-2-one in 3 ml of benzene is treated with 1.2 mmol of tributylphosphine and cooled to 0° C. 1.2 mmol of 1,1'-azo-bis(N,N-dimethyl formamide) are added. The reaction mixture is stirred for 24 hours at room temperature and then hexane is added. The mixture is filtered and the filtrate is evaporated. From the residue the title compound is identified by means of flash chromatography (SiO$_2$ 60F) on the basis of the Rf value.

g) 1-Benzyl-3-(2,4-dihydroxy-phenyl)-3-hydroxymethyl-piperidin-2-one

The title compound is obtained by a method analogous to that described in Example 2b, starting from 1-benzyl-3-2,4-dimethoxy-phenyl)-3-hydroxymethyl-piperidin-2-one and identified on the basis of the Rf value.

h) 1-Benzyl-3-(2,4-dimethoxy-phenyl-3-hydroxymethyl-piperidin-2-one

A solution of 1 mmol of 1-benzyl-3-(2,4-dimethoxy-phenyl)-2-oxo-piperidine-3-carboxylic acid methyl ester in 10 ml of methanol is treated with 2 mmol of sodium borohydride. The reaction mixture is stirred 30 minutes at room temperature and then quenched with saturated aqueous ammonium chloride solution. The methanol is evaporated. The residue is extracted with ethyl acetate (3×). The combined organic phases are dried with magnesium sulphate and evaporated. From the residue the title compound is identified by means of flash chromatography (SiO$_2$ 60F) on the basis of the Rf value.

i) 1-Benzyl-3-(2,4-dimethoxy-phenyl)-2-oxo-piperidine-3-carboxylic acid methyl ester A solution of 1 mmol of 1-benzyl-3-(2,4-dimethoxy-phenyl)-piperidin-2-one [597553-90-7] in 20 ml of tetrahydrofuran is cooled to −70° C. and treated drop wise with a solution of 1.2 mmol of lithium diisopropyl-amide in 5 ml of tetrahydrofuran. The mixture is stirred 15 minutes at −70° C. A solution of 1.2 mmol of methyl chloroformate in 5 ml of tetrahydrofuran is added at −70° C. and the reaction mixture is allowed to come to room temperature over a period of 7 hours. The reaction mixture is quenched with water and extracted with tert-butyl methyl ether (3×). The combined organic phases are dried with sodium sulphate and evaporated. From the residue the title compound is identified by means of flash chromatography (SiO$_2$ 60F) on the basis of the Rf value.

Example 9

2'-Oxo-2',3',6,7-tetrahydro-1'H,5H-spiro[imidazo[1,5-a]pyridine-84',4'-quinoline]-7'-carbonitrile The title compound is obtained by a method analogous to that described in Example 2, 2a and 2b, starting from 7'-methoxy-6,7-dihydro-1'H,5H-spiro[imidazo[1,5-a]pyridine-8,4'-quinolin]-2'(3'H)-one and identified on the basis of the Rf value.

The starting material is prepared as follows:

a) 7'-Methoxy-6,7-dihydro-1'H,5H-spiro[imidazo[1,5-a]pyridine-84'-quinolin]-2'(3'H-one A mixture of 1 mmol of (702) (Example 7c) and 2.8 g of dry ammonium acetate is heated in a dosed tube at 190° C. for 9 hours. The reaction mixture is cooled to room temperature and digested with water. From the residue the title compound is identified by means of flash chromatography (SiO$_2$ 60F) on the basis of the Rf value.

Alternative synthesis for 2'-oxo-2',3',6,7-tetrahydro-1'H,5H-spiro[imidazo[1,5-a]pyridine-8,4'-quinoline]-7'-carbonitrile 2'-Oxo-2',3',6,7-tetrahydro-1'H,5H-spiro[imidazo[1,5-a]pyridine-8,4'-quinoline]-7' carbonitrile A solution of 1 mmol of 3'-oxo-2',3',7,8-tetrahydro-6H-spiro[imidazo[1,5-a]pyridine-5,1'-indene]-5'-carbonitrile (Example 6) in 6 ml of acetonitrile is admixed at room temperature with 3 mmol of O-mesitylenesulphonylhydroxylamine and the mixture is subsequently stirred for 24 hours. The reaction mixture is evaporated. From the residue the title compound is identified by means of flash chromatography (SiO$_2$ 60F) on the basis of the Rf value.

Example 11

2'-Oxo-1',2',6,7-tetrahydro-5H-spiro[imidazo[1,5-a]pyridine-8,3'-indole]-6'-carbonitrile A solution of 1 mmol of methyl 6'-cyano-2'-oxo-6,7-dihydro-5H-spiro[imidazo[1,5-a]pyridine-8,3'-indole]-1'(2'H)-arboxylate in 14 ml of dimethyl sulphoxide and 1.4 ml of water is treated with 1.14 mmol of sodium cyanide and heated to 160° C. for 2 hours. The reaction mixture is cooled to room temperature and is evaporated. From the residue the title compound is identified by means of flash chromatography (SiO$_2$ 60F) on the basis of the Rf value.

The starting materials are prepared as follows:

a) Methyl 6'-cyano-2'-oxo-6,7-dihydro-5H-spiro[imidazo[1,5-a]pyridine-8,3'-indole]-1'(2'H)-carboxylate The title compound is obtained by a method analogous to that described in Example 2, 2a and 2b, starting from methyl 6'-methoxy-2'-oxo-6,7-dihydro-5H-spiro[imidazo[1,5-a]pyridine-8,3'-indole]-1'(2'H)-carboxylate and identified on the basis of the Rf value.

b) Methyl 6'-methoxy-2'-oxo-6,7-dihydro-5H-spiro[imidazo[1,5-a]pyridine-8,3'-indole]-1'(2'H)-carboxylate A solution of 1 mmol of 6'-methoxy-6,7-dihydro-5H-spiro[imidazo[1,5-a]pyridine-8,3'-indol]-2'(1'H)-one in 5 ml of N,N-dimethyl formamide is treated with 1.2 mmol of sodium hydride (60% dispersion in oil). The reaction mixture is stirred for 20 minutes at room temperature, then 1.2 mmol of methyl chloroformate are added. The reaction mixture is stirred for 20 minutes at room temperature, then diluted with water and extracted with tert-butyl methyl ether (3×). The combined organic phases are dried with sodium sulphate and evaporated. From the residue the title compound is identified by means of flash chromatography (SiO₂ 60F) on the basis of the Rf value.

c) 6'-Methoxy-6,7-dihydro-5H-spiro[imidazo[1,5-a]pyridine-8,3'-indol]-2'(1'H)-one A mixture of 1.9 mmol of 6'-methoxy-1,6,7,8a-tetrahydro-5H-spiro[imidazo[1,5-a]pyridine-8,3'-indol]-2'(1'H)-one and 3 g of manganese-dioxide in 50 ml of toluene is heated to reflux for 1.5 hours. The reaction mixture is cooled to room temperature, the solid is removed by filtration over Hyflo and the filtrate is evaporated. From the residue the title compound is identified by means of flash chromatography (SiO₂ 60F) on the basis of the Rf value.

d) 6'-Methoxy-1,6,7,8a-tetrahydro-5H-spiro[imidazo[1,5-a]pyridine-8,3'-indol]-2'(1'H)-one A solution of 31 mmol of 2'-(aminomethyl)-6-methoxyspiro[indole-3,3'-piperidin]-2(1H)-one and 31 mmol of N,N-dimethyl formamide dimethylacetal in 50 ml of dichloromethane is heated to reflux for 6 hours. The reaction mixture is cooled to room temperature and evaporated. From the residue the title compound is identified by means of flash chromatography (SiO₂ 60F) on the basis of the Rf value.

e) 2'-(Aminomethyl)-6-methoxyspiro[indole-3,3'-piperidin]-2(1H)-one 1 mmol of Di-tert-butyl 2'-(aminomethyl)-6-methoxy-2-oxo-1'H-spiro[indole-3,3'-piperidine]-1,1'(2H)-dicarboxylate are dissolved in 2 ml of dichloromethane and the solution is treated with 2 ml of trifluoroacetic acid. The reaction mixture is stirred at room temperature until no more starting material is observed and then poured into a saturated aqueous sodium bicarbonate solution. The phases are separated and the aqueous phase is extracted with dichloromethane (3×). The combined organic phases are washed with brine, dried with sodium sulphate and evaporated. From the residue the title compound is identified by means of flash chromatography (SiO₂ 60F) on the basis of the Rf value.

f) Di-tert-butyl 2'-(aminomethyl)-6-methoxy-2-oxo-1'H-spiro[indole-3,3'-piperidine]-1,1'(2 Hz dicarboxylate 1 mmol of Di-tert-butyl 2'-(azidomethyl)-6-methoxy-2-oxo-1'H-spiro[indole-3,3'-piperidine]-1,1'(2H)-dicarboxylate are dissolved in 5 ml of tetrahydrofuran. The solution is treated with 1.5 mmol of triphenylphosphine and a few drops of 25% ammonium hydroxide solution. The reaction mixture is stirred for 18 hours at room temperature and then evaporated. From the residue the title compound is identified by means of flash chromatography (SiO₂ 60F) on the basis of the Rf value.

g) Di-tert-butyl 2'-(azidomethyl-3-methoxy-2-oxo-1'H-spiro[indole-3,3'-piperidine]-1,1'(2H-dicarboxylate 10 mmol of Di-tert-butyl 6-methoxy-2'-[(methylsulphonyl)oxy]methyl)-2-oxo-1'H-spiro[indole-3,3'-piperidine]-1,1'(2H)-dicarboxylate are dissolved in 20 ml of N,N-dimethyl formamide and treated with 15 mmol of sodium azide. The reaction mixture is heated to 60° C. for 5 hours, then poured into water and extracted with tert-butyl methyl ether. The combined organic phases are washed with brine, dried with sodium sulfate and evaporated. From the residue the title compound is identified by means of flash chromatography (SiO₂ 60F) on the basis of the Rf value.

h) Di-tert-butyl 6-methoxy-2'-{[(methylsulphonyl)oxy]methyl}-2-oxo-1'H-spiro[indole-3,3'-piperidine]-1,1'(2H)-dicarboxylate A solution of 10 mmol of di-tert-butyl 2'-(hydroxymethyl)-6-methoxy-2-oxo-1'H-spiro[indole-3,3'-piperidine]-1,1'(2H)-dicarboxylate in 30 ml dichloromethane is cooled to 0° C. and treated with 15 mmol of triethylamine, followed by 11 mmol of methanesulphonyl chloride. The reaction mixture is stirred at 0° C. for 1 hour and then at room temperature for 1 hour. The reaction mixture is poured into an aqueous saturated sodium bicarbonate solution and extracted with dichloromethane (3×). The combined organic phases are washed with brine, dried with sodium sulphate and evaporated. From the residue the title compound is identified by means of flash chromatography (SiO₂ 60F) on the basis of the Rf value.

i) Di-tert-butyl 2'-(hydroxymethyl)-6-methoxy-2-oxo-1'H-spiro[indole-3,3'-piperidine]-1,1'(2H)-dicarboxylate A solution of 1 mmol di-tert-butyl 2'-({[tert-butyl(dimethyl)silyl]oxy}methyl)-6-methoxy-2-oxo-1'H-spiro[indole-3,3'-piperidine]-1,1'(2H)-dicarboxylate in 5 ml of tetrahydrofuran is treated with 1.5 mmol of tetrabutylammonium fluoride (1M solution in tetrahydrofuran) and the solution is stirred for 1 hour at room temperature. The reaction mixture is diluted with water and extracted with tert-butyl methyl ether (3×). The combined organic phases are dried with sodium sulphate and evaporated. From the residue the title compound is identified by means of flash chromatography (SiO₂ 60F) on the basis of the Rf value.

j) Di-tert-butyl 2'-({[tert-butyl(dimethyl)silyl]oxy}methyl)-6-methoxy-2-oxo-1'H-spiro[indole-3,3'-piperidine]-1,1'(2H)-dicarboxylate A solution of 1 mmol of tert-butyl 2'-({[tert-butyl(dimethyl)silyl]oxy}methyl)-6-methoxy-2-oxospiro[indole-3,3'-piperidine]-1(2H)carboxylate in 5 ml acetonitrile is treated with 2.2 mmol of N,N-dimethylaminopyridine and 2.2 mmol of di-tert-butyl dicarbonate. The reaction mixture is stirred for 48 hours at room temperature, then poured into water and extracted with tert-butyl methyl ether (3×). The combined organic phases are washed with brine, dried with sodium sulphate and evaporated. From the residue the title compound is identified by means of flash chromatography (SiO₂ 60F) on the basis of the Rf value.

k) Tert-butyl 2'-({[tert-butyl(dimethyl)silyl]oxy}methyl)-6-methoxy-2-oxospiro[indole-3,3'-piperidine]-1(2H)-carboxylate A solution of 1 mol of 3-(3-amino-propyl)-6-methoxy-1,3-dihydro-indol-2-one in 5 ml of ethanol is treated with 5 mmol of sodium acetate hydrochloride and 5 mmol of (tert-butyl-dimethyl-silanyloxy)-acetaldehyde [102191-92-4] and stirred at 60° C. for 3 hours. The reaction mixture is concentrated in vacuo and treated with aqueous saturated potassium carbonate solution and diethyl ether. The phases are separated and the aqueous phase is extracted with diethyl ether (2×).

The combined organic phases are washed with water, dried with sodium sulphate and evaporated. From the residue the title compound is identified by means of flash chromatography (SiO$_2$ 60F) on the basis of the Rf value.

l) 3-(3-Amino-propyl)-6-methoxy-1,3-dihydro-indol-2-one hydrochloride

A solution of 30 mmol of 3-(6-methoxy-1H-indol-3-yl)-ypropylamine [105338-78-1] in 6.5 ml of dimethyl sulphoxide is cooled to 0° C. and 3.8 ml of conc. HCl are added drop wise. The mixture is stirred at room temperature over night and then diluted with 50 ml of ethanol. The mixture is stirred for 1 hour, and then cooled to 4° C. for several hours. The crystals are filtered off, washed with ethanol and diethyl ether and dried. The title compound is identified on the basis of the Rf value Example 12

2'-Oxo-2',3',5,6-tetrahydro-1'H-spiro[cyclopena[c]pyridine-7,4'-quinoline]-7'-carbonitrile The title compound is obtained by a method analogous to that described in Example 2 and 2a, starting from 7'-hydroxy-5,6-dihydro-1'H-spiro[cyclopenta[c]pyridine-7,4'-quinolin]-2'(3'H)-one and identified on the basis of the Rf value.
The starting materials are prepared as follows:

a) 7'-Hydroxy-5,6-dihydro-1'H-spiro[cyclopenta[c]pyridine-7,4'-quinolin]-2'(3'H)-one The title compound is obtained by a method analogous to that described in Example 2b, starting from 7'-hydroxy-5,6-dihydro-1'H-spiro[cyclopenta[c]pyridine-7,4'-quinolin]-2'(3H)-one and/or 7'-methoxy-5,6-dihydro-1'H-spiro[cyclopenta[c]pyridine-7,4'-quinolin]-2'(3'H)-one and identified on the basis of the Rf value.

b) 7'-Methoxy-5,6-dihydro-1'H-spiro[cyclopenta[c]pyridine-7,4'-quinolin]-2'(3'H)-one and/or 7'-Hydroxy-5,6-dihydro-1'H-spiro[cyclopenta[c]pyridine-7,4'-quinolin]-2'(3'H)-one 5 mmol of 2-(7-hydroxy-6,7-dihydro-5H-[2]pyridin-7-yl)-N-(3-methoxyphenyl)acetamide are charged to a polyethylene vessel and admixed with 50 ml of HF. The vessel is sealed and the reaction solution is left to stand at room temperature for 16 h. The excess HF is removed by means of a stream of argon and the residue is taken up in diethyl ether. The solution is washed cautiously with saturated aqueous sodium hydrogen carbonate solution, dried with sodium sulphate and evaporated. From the residue the title compound is identified by means of flash chromatography (SiO$_2$ 60F) on the basis of the Rf value.

c) 2-(7-Hydroxy-6,7-dihydro-5H-[2]pyridin-7-yl)-N-(3-methoxyphenyl)acetamide

A solution of 50 mmol of N-(3-methoxyphenyl)acetamide [588-16-9] in 200 ml of tetrahydrofuran is cooled to −40° C. 110 mmol of butyllithium (1.6M in hexane) are added dropwise at −40-30° C. and the reaction mixture is subsequently stirred at 0° C. for 1 hour. The mixture is cooled again to 40° C. and a solution of 50 mmol of 5,6-dihydro[2]pyridin-7-one [51907-18-7] in 50 ml of tetrahydrofuran is added dropwise at this temperature. The reaction mixture is stirred at 0° C. for 2-4 h and then poured into saturated aqueous ammonium chloride solution. The mixture is extracted with tert-butyl methyl ether and the combined organic extracts are washed with brine, dried with sodium sulphate and evaporated. From the residue the title compound is obtained by means of flash chromatography (SiO$_2$ 60F) on the basis of the Rf value.

Example 13

3'-Oxo-2',3',6,7-tetrahydro-5H-spiro[imidazo[1,5-a]pyridine-8,1'-isoindole]-5'-carbonitrile A solution of 1 mmol of 5-cyano-2-[8-(2-methyl-propane-2-sulphinylamino)-5,6,7,8-tetrahydro-imidazo[1,5-a]pyridin-8-yl]-benzoic acid tert-butyl ester in 6 ml of methanol is treated with 6 ml of 4M HCl in dioxan and stirred 6 hours at room temperature. The mixture is evaporated and the residue is dissolved in 20 ml of dichloromethane. 5.0 mmol of triethylamine and 1.0 mmol of tri-propylphosphonic acid cyclic anhydride [68957-94-8] (50% in ethyl acetate) are added at room temperature. The reaction mixture is stirred for 2 hours, diluted with dichloromethane, washed with 1M HCl and brine. The organic phase is dried over sodium sulphate and concentrated under reduced pressure. From the residue the title compound is identified by means of flash chromatography (SiO$_2$ 60F) on the basis of the Rf value.
The starting materials are prepared as follows:

a) 5-Cyano-2-[8-(2-methyl-propane-2-sulphinylamino-5,6,7,8-tetrahydro-imidazo[1,5-a]pyridin-8-yl]-benzoic acid tert-butyl ester In a dried flask under Ar atmosphere are placed 1.05 mmol of isopropylmagnesium chloride.lithium chloride in tetrahydrofuran solution (prepared from magnesium, dry lithium chloride and isopropyl chloride in THF according to A. Krasovskiy and P. Knochel; Angewandte Chemie International Edition 2004, 43, 3333-3336). The solution is cooled to −15° C. and 1 mmol of 5-cyano-2-iodo-benzoic acid tert-butyl ester is added in one portion. The reaction mixture is stirred for 15 minutes at −10° C. and then 0.02 ml of a copper (I) cyanide.2 lithium chloride solution (1.0M in tetrahydrofuran) as well as 1.1 mmol of 2-methyl-propane-2-sulphinic acid [6,7-dihydro-5H-imidazo[1,5-a]pyridin-(8E)-ylidene]-mide are added. The reaction mixture is stirred for 1 hour at 0° C., then quenched by addition of aqueous saturated ammonium chloride solution and extracted with diethyl ether (3×). The combined organic phases are washed with brine, dried with sodium sulphate and evaporated. From the residue the title compound is identified by means of flash chromatography (SiO$_2$ 60F) on the basis of the Rf value.

b) 2-Methyl-propane-2-sulphinic acid [6,7-dihydro-5H-imidazo[1,5-a]pyridin-(8E)-ylidene]-amide A mixture of 1 mmol of 6,7-dihydro-5H-imidazo[1,5-a]pyridine-8-one [426219-51-4] and 1.2 mmol of 2-methyl-propan-2-sulphinic acid amid is treated dropwise with 0.35 ml of titanium-tetra-isopropoxide. The reaction mixture is stirred at room temperature for 36 hours, then poured into 5 ml of brine and 10 ml of ethyl acetate and stirred vigorously for 10 minutes. The reaction mixture is filtered over Hyflo and the filtrate is evaporated. From the residue the title compound is identified by means of flash chromatography (SiO$_2$ 60F) on the basis of the Rf value.

c) 5-Cyano-2-iodo-benzoic acid tert-butyl ester 8.9 mmol of 5-Cyano-2-iodo-benzoic acid [219841-92-6] is heated at reflux with 6 ml of thionyl-chloride and 1 drop of N,N-dimethylformamide until all the solid dissolves and there is no further gas evolution. The solution is cooled to room temperature and evaporated to dryness. The residue is treated with 32 mmol of dry tert-butyl alcohol and 49 mmol of dry pyridine in 5 ml of chloroform at 0° C. under an Ar atmosphere. After the addition, the mixture is refluxed overnight, cooled, and evaporated to dryness. From the residue the title compound is identified by means of flash chromatography (SiO$_2$ 60F) on the basis of the Rf value.

Example 14

3'-Oxo-3',4',6,7-tetrahydro-2'H,5H-spiro[imidazo[1,5-a]pyridine-8,1'-isoquinoline]-6'-carbonitrile The title compound is obtained by a method analogous to that described in Example 12, starting from {5-cyano-2-[8-(2-methyl-propane-2-sulphinylamino)-5,6,7,8-tetrahydro-imidazo[1,5-a]pyridin-8-yl]-phenyl}acetic acid and identified on the basis of the Rf value.

The starting materials are prepared as follows:

a1) {5-Cyano-2-[8-(2-methyl-propane-2-sulphinylamino)-5,6,7,8-tetrahydro-imidazo[1,5-a]pyridin-8-yl]-pheny}acetic acid A solution of 1 mmol of 5-cyano-2-[8-(2-methyl-propane-2-sulphinylamino)-5,6,7,8-tetrahydro-imidazo[1,5-a]pyridin-4-yl]-benzoic acid in 10 ml of dichloromethane is treated with 2 mmol of oxalyl chloride. The reaction is stirred for 45 minutes at room temperature and then N,N-dimethylformamide (1 drop) is added. After stirring for 15 minutes, the solution is cooled to room temperature and evaporated to dryness. The residue is dissolved in 10 ml of dry dichloromethane and evaporated. The residue is taken up in dry tetrahydrofuran and cooled to 0° C. The solution is treated with a solution of diazomethane in diethyl ether (1.5%) and stirred for 3 hours at 0° C. and overnight at room temperature. The reaction mixture is diluted with tert-butyl methyl ether and the organic phase is washed with water and brine, dried over sodium sulphate and concentrated under reduced pressure. The residue is dissolved in 10 ml of tetrahydrofuran under exclusion of light. The solution is cooled to −15° C. and treated with a solution of silver trifluoroacetate (0.22M in triethylamine) in several portions until complete conversion is reached. The reaction mixture is evaporated and the residue is taken up in 0.1 M NaOH—the aqueous phase is washed with tert-butyl methyl ether, then acidified with 2M HCl and extracted with ethyl acetate (1×) and with tert-butyl methyl ether (2×). The combined organic phases are washed with brine, dried with sodium sulphate and evaporated. From the residue the title compound is identified by means of flash chromatography (SiO$_2$ 60F) on the basis of the Rf value.

b1) 5-Cyano-2-[8-(2-methyl-propane-2-sulphinylamino)-5,6,7,8-tetrahydro-imidazo[1,5-a]pyridin-8-yl]-benzoic acid A stirred solution of 2 mmol of 5-cyano-2-[8-(2-methyl-propane-2-sulphinylamino)-5,6,7,8-tetrahydro-imidazo[1,5-a]pyridin-8-yl]-benzoic acid tert-butyl ester (Example 13a) in 50 ml of dichloromethane is cooled to −10° C. 8 mmol of titanium tetrachloride are slowly added and the temperature is brought to 0° C. After stirring for 2 hours, a chilled 2M solution of HCl is added. The organic phase is separated, washed with 2M HCl (3×), brine (2×) and concentrated under reduced pressure. From the residue the title compound is identified by means of flash chromatography (SiO$_2$ 60F) on the basis of the Rf value.

Alternative synthesis for 3'-oxo-3',4',6,7-tetrahydro-2'H, 5H-spiro[imidazo[1,5-a]pyridine-8,1'-isoquinoline]-6'-carbonitrile

3'-Oxo-3',4',6,7-tetrahydro-2'H,5H-spiro[imidazo[1,5-a]pyridine-8,1'-isoquinoline]-6'-carbonitrile 1 mmol of 3-Cyanomethyl-4-(8-hydroxy-5,6,7,8-tetrahydro-imidazo[1,5-a]pyridin-8-yl)-benzonitrile is added to a solution of 3 ml of methanesulphonic acid at 0° C. The reaction mixture is stirred at room temperature for 8 hours, then quenched with ice water. The aqueous phase is extracted with dichloromethane (3×) and the combined organic extracts are dried over magnesium sulphate and evaporated. From the residue the title compound is identified by means of flash chromatography (SiO$_2$ 60F) on the basis of the Rf value.

The starting materials are prepared as follows:

a2) 3-Cyanomethyl-4-(8-hydroxy-5,6,7,8-tetrahydro-imidazo[1,5-a]pyridin-8-yl)-benzonitrile In a dried flask under Ar atmosphere are placed 1.05 mmol of isopropylmagnesium chloride.lithium chloride in tetrahydrofuran solution (prepared from magnesium, dry lithium chloride and isopropyl chloride in THF according to A. Krasovskiy and P. Knochel; Angewandte Chemie International Edition 2004, 43, 3333-3336). The solution is cooled to −15° C. and 1 mmol of 3-cyanomethyl-4-iodo-benzonitrile is added in one portion. The reaction mixture is stirred for 15 minutes at −10° C. and 0.02 ml of a copper (I) cyanide.2 lithium chloride solution (10M in tetrahydrofuran) as well as 1.1 mmol of 6,7-dihydro-5H-imidazo[1,5-a]pyridin-8-one [426219-51-4] are added. The reaction mixture is stirred for 1 hour at 0° C., then quenched by addition of aqueous saturated ammonium chloride solution and extracted with diethyl ether (3×). The combined organic phases are washed with brine, dried with sodium sulphate and evaporated. From the residue the title compound is identified by means of flash chromatography (SiO$_2$ 60F) on the basis of the Rf value.

b2) 3-Cyanomethyl-4-iodo-benzonitrile 2 mmol of Sodium nitrite in 5 ml water is added dropwise over 10 minutes to a stirred solution of 2 mmol of 4-amino-3-cyanomethyl-benzonitrile in 6 ml of water and 3 ml of conc. sulphuric acid at 0° C. After a further 15 minutes at 5° C., a solution of 3.9 mmol of potassium iodide in 6 ml of water is quickly added and the mixture allowed to warm to room temperature. 10% Aqueous sodium thiosulphate is added, the mixture is extracted with ethyl acetate, the extract is dried over magnesium sulphate and evaporated. From the residue the title compound is identified by means of flash chromatography (SiO$_2$ 60F) on the basis of the Rf value.

c) 4-Amino-3-cyanomethyl-benzonitrile 2 mmol of (2-Amino-5-bromo-phenyl)-acetonitrile [882855-95-0] and 4 mmol of copper (I) cyanide are heated at 200° C. in 2 ml of N-methylpyrrolidinone for 4 h. After cooling to room temperature, the solution is diluted with water and extracted with ethyl acetate (3×). The organic layer is separated, dried over magnesium sulphate and evaporated.

From the residue the title compound is identified by means of flash chromatography (SiO$_2$ 60F) on the basis of the Rf value.

Example 15

2'-Methyl-3'-oxo-2',3',6,7-tetrahydro-5H-spiro[imidazo[1,5-a]pyridine-8,1'-isoindole]-5'-carbonitrile A solution of 1 mmol of 3'-oxo-2',3',6,7-tetrahydro-5H-spiro[imidazo[1,5-a]pyridine-8,1'-isoindole]-5'-carbonitrile (Example 13) in 5 ml of N,N-dimethylformamide is treated with 1.2 mmol of sodium hydride (60% dispersion in oil). The reaction mixture is stirred for 20 minutes at room temperature, and then 1.2 mmol of methyl iodide are added. The reaction mixture is stirred for 20 minutes at room temperature, then diluted with water and extracted with tert-butyl methyl ether (3×). The combined organic phases are dried with sodium sulphate and evaporated. From the residue the title compound is identified by means of flash chromatography (SiO$_2$ 60F) on the basis of the Rf value.

The compound below is prepared by methods analogous to those described in Example 15:

16 2'-Methyl-3'-oxo-3',4',6,7-tetrahydro-2'H,5H-spiro[imidazo[1,5-a]pyridine-8,1'-isoquinoline]-6'-carbonitrile Example 17

2',3',6,7-Tetrahydro-5H-spiro[imidazo[1,5-a]pyridine-8,1'-isoindole]-5'-carbonitrile To a solution of 1.0 mmol of 3'-oxo-2',3',6,7-tetrahydro-5H-spiro[imidazo[1,5-a]pyridine-8,1'-isoindole]-5'-carbonitrile (Example 13) in 10 ml of tetrahydrofuran are added 3.0 mmol of a solution of borane-tetrahydrofuran complex (1M in tetrahydrofuran). The reaction mixture is stirred over night at 50° C., then cooled to room temperature and quenched carefully with 10 ml of methanol. After the gas evolution ceases, the reaction mixture is evaporated. From the residue the title compound is identified by means of flash chromatography (SiO$_2$ 60F) on the basis of the Rf value.

The compounds below are prepared by methods analogous to those described in Example 17:

18 3',4',6,7-Tetrahydro-2'H,5H-spiro[imidazo[1,5-a]pyridine-8,1'-isoquinoline]-6'-carbonitrile starting from 3'-oxo-3',4',6,7-tetrahydro-2'H,5H-spiro[imidazo[1,5-a]pyridine-8,1'-isoquinoline]-6'-carbonitrile (Example 14).

19 2'-Methyl-2',3',6,7-tetrahydro-5H-spiro[imidazo[1,5-a]pyridine-8,1'-isoindole]-5'-carbonitrile starting from 2'-methyl-3'-oxo-2',3',6,7-tetrahydro-5H-spiro[imidazo[1,5-a]pyridine-8,1'-isoindole]-5'-carbonitrile (Example 15).

20 2'-Methyl-3',4',6,7-tetrahydro-2'H,5H-spiro[imidazo[1,5-a]pyridine-8,1'-isoquinoline]-6'-carbonitrile starting from 2'-methyl-3'-oxo-3',4',6,7-tetrahydro-2H,5H-spiro[imidazo[1,5-a]pyridine-8,1'-isoquinoline]-6'-carbonitrile (Example 16).

The invention claimed is:
1. A compound of the general formula

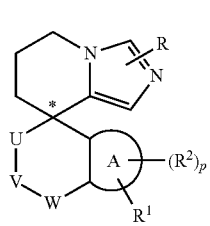

(Id')

having a specific configuration at the asymmetric carbon atom labeled "*", in which A is aryl;

U is —C(R$^3$)(R$^4$)—, S(O)$_m$—, —N(R$^5$)— or a bond;

V is —C(R$^3$)(R$^4$)— or
  a) if U is either a bond or —C(R$^3$)(R$^4$)—, V is alternatively —S(O)$_m$— or —N(R$^5$)—,
  b) if U is —S(O)$_m$—, V is alternatively —N(R$^5$)—, or
  c) if U is —N(R$^5$)—, V is alternatively —S(O)$_m$—;

W is —C(R$^3$)(R$^4$)— or
  a) if U is either a bond or —C(R$^3$)(R$^4$)— and V is —C(R$^3$)(R$^4$)—, W is alternatively —O—, —S(O)$_m$— or —N(R$^5$)—,
  b) if U is either a bond or —C(R$^3$)(R$^4$)— and V is —S(O)$_m$—, W is alternatively —N(R$^5$)—,
  c) if U is either a bond or —C(R$^3$)(R$^4$)— and V is —N(R$^5$)—, W is alternatively —S(O)$_m$—, or
  d) if U is —N(R$^5$)— and V is —C(O)—, W is alternatively —N(R$^5$)—;

R is hydrogen, $C_1$-$C_8$-alkyl, $C_1$-$C_8$-alkoxy-$C_0$-$C_4$-alkyl, halogen, tri-$C_1$-$C_4$-alkylsilyl, deuterium or trifluoromethyl;

R$^1$ is $C_1$-$C_8$-alkyl, $C_0$-$C_8$-alkylcarbonyl, amino, mono- or di-$C_1$-$C_8$-alkylamino, $C_0$-$C_8$-alkyl-carbonylamino, $C_0$-$C_8$-alkylcarbonyl-$C_1$-$C_8$-alkylamino, carbamoyl, mono- or di-$C_1$-$C_8$-alkyl-aminocarbonyl, carboxyl, carboxy-$C_1$-$C_4$-alkyl, halogen, cyano, oxo, trifluoromethyl, trifluoromethoxy, $C_1$-$C_8$-alkoxy, or $C_1$-$C_8$-alkoxycarbonyl, which radicals may be substituted by 1-4 $C_1$-$C_8$-alkyl, $C_0$-$C_8$-alkylcarbonyl, halogen, cyano, oxo, trifluoromethyl, $C_0$-$C_8$-alkylcarbonylamino, $C_0$-$C_8$-alkylcarbonyl-$C_1$-$C_8$-alkylamino, carbamoyl, mono- or di-$C_1$-$C_8$-alkylaminocarbonyl, carboxy-$C_0$-$C_4$-alkyl, $C_1$-$C_8$-alkoxy, or $C_1$-$C_8$-alkoxycarbonyl, R$^2$ is hydrogen, $C_1$-$C_8$-alkyl, $C_0$-$C_8$-alkylcarbonyl, amino, mono- or di-$C_1$-$C_8$-alkylamino, $C_0$-$C_8$-alkylcarbonylamino, $C_0$-$C_8$-alkylcarbonyl-$C_1$-$C_8$-alkylamino, carbamoyl, mono- or di-$C_1$-$C_8$-alkylaminocarbonyl, carboxyl, carboxy-$C_1$-$C_4$-alkyl, halogen, cyano, oxo, trifluoromethyl, trifluoromethoxy, $C_1$-$C_8$-alkoxy, or $C_1$-$C_8$-alkoxycarbonyl, which radicals may be substituted by 1-4 $C_1$-$C_8$-alkyl, $C_0$-$C_8$-alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- or di-$C_1$-$C_8$-alkylaminocarbonyl, carboxy-$C_0$-$C_4$-alkyl, $C_1$-$C_8$-alkoxy, or $C_1$-$C_8$-alkoxycarbonyl;

$R^3$ is hydrogen or $C_1$-$C_8$-alkyl;
$R^4$ a) is hydrogen or $C_1$-$C_8$-alkyl; or
 b) together with $R^3$ is oxo;
$R^5$ is hydrogen, $C_1$-$C_8$-alkyl or $C_0$-$C_8$-alkylcarbonyl;
m is a number 0, 1 or 2;
p is is a number 1;
or its pharmaceutically useful salt.

2. A compound according to claim 1, wherein R is hydrogen or deuterium.

3. A compound according to claim 1, wherein $R^1$ is $C_1$-$C_8$-alkyl, $C_0$-$C_8$-alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- or di-$C_1$-$C_8$-alkylaminocarbonyl, carboxy-$C_0$-$C_4$-alkyl, $C_1$-$C_8$-alkoxy, or $C_1$-$C_8$-alkoxycarbonyl.

4. A compound according to claim 1, wherein $R^2$ is hydrogen, halogen, cyano, trifluoromethyl, trifluoromethoxy, or $C_1$-$C_{1-8}$-alkyl.

5. A compound according to claim 1, wherein
R is hydrogen or deuterium;
$R^1$ is formyl, acetyl, halogen, or cyano; and
$R^2$ is, independently of one another, hydrogen, halogen, cyano or, $C_1$-$C_8$-alkyl.

6. A pharmaceutical composition comprising a compound of the general formula (I) according to claim 1 and conventional excipients.

7. A pharmaceutical combination in the form of a product or kit composed of individual components consisting a) of a compound of the formula (I) according to claim 1 and b) of at least one pharmaceutical form whose active ingredient has a blood pressure-lowering, an inotropic, a metabolic or a lipid-lowering effect.

8. A compound according to claim 3, wherein $R^1$ is formyl, acetyl, or cyano.

9. A compound according to claim 4, wherein $R^2$ is hydrogen, halogen, cyano or $C_1$-$C_8$-alkyl.

* * * * *